US009909124B2

(12) United States Patent
Crooke et al.

(10) Patent No.: US 9,909,124 B2
(45) Date of Patent: Mar. 6, 2018

(54) COMPOUNDS AND METHODS FOR MODULATING APOLIPOPROTEIN C-III EXPRESSION FOR IMPROVING A DIABETIC PROFILE

(71) Applicant: ISIS PHARMACEUTICALS, INC., Carlsbad, CA (US)

(72) Inventors: Rosanne M. Crooke, Carlsbad, CA (US); Veronica J. Alexander, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/900,320

(22) PCT Filed: Jun. 23, 2014

(86) PCT No.: PCT/US2014/043723
§ 371 (c)(1),
(2) Date: Dec. 21, 2015

(87) PCT Pub. No.: WO2014/205449
PCT Pub. Date: Dec. 24, 2014

(65) Prior Publication Data
US 2016/0152974 A1 Jun. 2, 2016

Related U.S. Application Data

(60) Provisional application No. 61/838,211, filed on Jun. 21, 2013.

(51) Int. Cl.
*C12N 15/113* (2010.01)
*A61K 31/155* (2006.01)
*A61K 31/713* (2006.01)

(52) U.S. Cl.
CPC .......... *C12N 15/113* (2013.01); *A61K 31/155* (2013.01); *A61K 31/713* (2013.01); *C12N 2310/11* (2013.01); *C12N 2310/315* (2013.01); *C12N 2310/321* (2013.01); *C12N 2310/3231* (2013.01); *C12N 2310/3341* (2013.01); *C12N 2310/341* (2013.01)

(58) Field of Classification Search
CPC .................................................. C12N 15/113
See application file for complete search history.

(56) References Cited

U.S. PATENT DOCUMENTS

| | | | |
|---|---|---|---|
| 4,981,957 A | 1/1991 | Lebleu et al. |
| 5,034,506 A | 7/1991 | Summerton et al. |
| 5,118,800 A | 6/1992 | Smith et al. |
| 5,166,315 A | 11/1992 | Summerton et al. |
| 5,185,444 A | 2/1993 | Summerton et al. |
| 5,319,080 A | 6/1994 | Leumann |
| 5,359,044 A | 10/1994 | Cook et al. |
| 5,393,878 A | 2/1995 | Leumann |
| 5,446,137 A | 8/1995 | Maag et al. |
| 5,466,786 A | 11/1995 | Buhr et al. |
| 5,514,785 A | 5/1996 | Van Ness et al. |
| 5,519,134 A | 5/1996 | Acevedo et al. |
| 5,567,811 A | 10/1996 | Misiura et al. |
| 5,576,427 A | 11/1996 | Cook et al. |
| 5,591,722 A | 1/1997 | Montgomery et al. |
| 5,597,909 A | 1/1997 | Urdea et al. |
| 5,610,300 A | 3/1997 | Altmann et al. |
| 5,627,053 A | 5/1997 | Usman et al. |
| 5,639,873 A | 6/1997 | Barascut et al. |
| 5,646,265 A | 7/1997 | McGee |
| 5,670,633 A | 9/1997 | Cook et al. |
| 5,698,685 A | 12/1997 | Summerton et al. |
| 5,700,920 A | 12/1997 | Altmann et al. |
| 5,792,847 A | 8/1998 | Buhr et al. |
| 6,268,490 B1 | 7/2001 | Imanishi et al. |
| 6,525,191 B1 | 2/2003 | Ramasamy |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,399,845 B2 | 7/2008 | Seth et al. |
| 7,427,672 B2 | 9/2008 | Imanishi et al. |
| 7,598,227 B2 | 10/2009 | Crooke et al. |
| 7,750,141 B2 | 7/2010 | Crooke et al. |
| 8,530,439 B2 | 9/2013 | Crooke et al. |
| 2004/0171570 A1 | 9/2004 | Allerson et al. |

(Continued)

FOREIGN PATENT DOCUMENTS

WO WO 1998/039352 9/1998
WO WO 1999/014226 3/1999

(Continued)

OTHER PUBLICATIONS

European Search Report for EP 14813708.6 dated Jan. 23, 2017.
Albaek, et al., "Analogues of a Locked Nucleic Acid with Three-Carbon 2', 4'-Linkages: Synthesis by Ring-Closing Metathesis and Influence of Nucleic Acid Duplex Stability" J. Org. Chem. (2006) 71:7731-7740.
Altmann et al., "Second generation antisense oligonucleosides—inhibition of PKC-a an c-RAF kinase expression by chimeric oligonucleotides incorporating 5'-substitute carbocyclic nucleosides and 2'-O-ethylene glycol substituted ribonucleosides." Nucleosides Nucleotides (1997) 16(7-9: 917-926.

(Continued)

Primary Examiner — J. E. Angell
(74) Attorney, Agent, or Firm — Grant IP

(57) ABSTRACT

Provided herein are improved compounds, compositions and associated methods for reducing expression of ApoCIII mRNA and protein in a subject having, or at risk of having, diabetes. Also provided herein are compounds, compositions and associated methods improving peripheral insulin sensitivity, a lipid profile and a diabetes profile as well as reducing free fatty acids and intramyocellular triglyceride deposition.

29 Claims, No Drawings

(56) References Cited

U.S. PATENT DOCUMENTS

| | | |
|---|---|---|
| 2004/0208856 A1 | 10/2004 | Crooke et al. |
| 2004/0224304 A1 | 11/2004 | Berggren |
| 2005/0130923 A1 | 6/2005 | Bhat et al. |
| 2006/0264395 A1* | 11/2006 | Crooke ................ C12N 15/113 514/44 A |
| 2007/0287831 A1 | 12/2007 | Seth et al. |
| 2008/0039618 A1 | 2/2008 | Allerson et al. |
| 2009/0081201 A1 | 3/2009 | Breggren |
| 2011/0060030 A1 | 3/2011 | Crooke et al. |
| 2012/0129911 A1* | 5/2012 | Sacks ................ A61K 31/7088 514/44 A |
| 2013/0317085 A1 | 11/2013 | Crooke et al. |
| 2014/0128453 A1 | 5/2014 | Mullick et al. |
| 2015/0045431 A1 | 2/2015 | Amarin |

FOREIGN PATENT DOCUMENTS

| | | |
|---|---|---|
| WO | WO 2003/004602 | 1/2003 |
| WO | WO 2004/093783 | 11/2004 |
| WO | WO 2004/097429 | 11/2004 |
| WO | WO 2004/106356 | 12/2004 |
| WO | WO 2005/021570 | 3/2005 |
| WO | WO 2005/121371 | 12/2005 |
| WO | WO 2006/047842 | 5/2006 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2010/036696 | 4/2010 |
| WO | WO 2010/036698 | 4/2010 |
| WO | WO 2010/083615 | 7/2010 |
| WO | WO 2010/107838 | 9/2010 |
| WO | WO 2011/017521 | 2/2011 |
| WO | WO 2012/149495 | 11/2012 |
| WO | WO 2012/177947 | 12/2012 |

OTHER PUBLICATIONS

Altmann et al., "Second Generation of Antisense Olignucleotides: From Nuclease Resistance to Biological Efficacy in Animals" Chimia (1996) 50: 168-176.

Altmann et al., "Second-generation antisense oligonucleotides: structure-activity relationships and the design of improved signal-transduction inhibitors" Biochem. Soc. Trans. (1996) 24: 630-637.

Altschul et al., "Basic Local Alignment Search Tool" J. Mol. Biol. (1990) 215:403-410.

American Diabetes Association "Standards of Medical Care in Diabetes—2008" Diabetes Care (2008) 31:S12-S54.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem., (1997) 272(18): 11944-12000.

Braasch et al., "Locked nucleic acid (LNA): fine-tuning the recognition of DNA and RNA" Chem. Biol. (2001) 8: 1-7.

Braasch et al., "Novel Antisense and Peptide Nucleic Acid Strategies for Controlling Gene Expression" Biochem. (2002) 41(14):4503-4510.

Catapano et al., "ESC/EAS guidelines for the management of dyslipidaemias: the task force for the management of dyslipidaemias of European Society of Cardiology (ESC) and the European Athersclerosis Societ (EAS)" (2011) Atherosclerosis 217S:S1-S44.

Chan et al., "Markers of triglyceride-rich lipoprotein remnant metabolism in visceral obesity." Clinical Chemistry (2002) 278-283.

Chan et al., "An ABC of apolipoprotein C-III: a clinically useful new cardiovascular risk factor?" International Journal of Clinical Practice (2008) 62:799-809.

Chin "On the Preparation and Utilization fo Isolated and Purified Oligonucleotides" Document purportedly located on a CD-ROM and contributed to the public collection of the Katherine R. Everett Law Library of the University of North Carolia on Mar. 14, 2002.

Davidsson "A proteomic study of the apolipoproteins in LDL subclasses in patients with the metabolic syndrome and type 2 diabetes." Journal of lipid research (2005) 46:1999-2006.

Duivenvoorden et al., "Apolipoprotein C3 Deficiency Results in Diet-Induced Obesity and Aggravated Insulin Resistance in Mice" Diabetes (2005) 54:664-671.

Elayadi et al., "Application of PNA and LNA oligomers to chemotherapy" Curr. Opinion Invest. Drugs (2001) 2: 558-561.

Faerch et al., "The disposition index: adjustment for peripheral vs. hepatic insulin sensitivity?" Journal of Physiology (2010) 588:759-764.

Fredrickson et al., "A System for Phenotyping Hypolipoproteinemia." Circulation (1965) 31:321-327.

Fredrickson et al., "Fat transport in lipoproteins—an integrated approach to mechanisms and disorders." New England Journal of Medicine (1967)276:34-42.

Freer et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21): 6365-6372.

Gaudet et al., "Review of the clinical development of alipogene tiparvovec gene therapy for lipoprotein lipase deficiency" Atherosclerosis Supplements (2010) 11: 55-60.

Gautschi et al. "Activity of a Novel bcl-2/bcl-xL-Bispecific Antisense Oligonucleotide Against Tumors of Diverse Histologic Origins" J. Natl. Cancer Inst. (2001) 93:463-471.

GenBank Accession No. NT_035088.1, Aug. 1, 2002, from the NCBI website: http://www.ncbi.nlm.nih.gov/nuccore/NT_035088.1?report=genbank, printout on Jan. 16, 2014.

Goodman, "Report of the National Cholesterol Education Program Expert Panel on Detection, Evaluation, and treatment of high blood cholesterol in adults" Arch Intern Med (1988) 148: 36-39.

Gordon et al., "High density lipoprotein as a protective factor against coronary heart disease. The Framingham Study." American Journal of Medicine (1977) 62:707-714.

Gu et al. "Base Pairing Properties of D- and L-Cyclohexene Nucleic Acids (CeNA)" Oligonucleotides (2003) 13(6): 479-489.

Gu et al., "Enzymatic resolution and base pairing properties of D- and L-cyclohexenyl nucleic acids (CeNA)." Nucleosides, Nucleotides & Nucleic Acids (2005) 24(5-7): 993-998.

Gu et al., "Synthesis of enantiomeric-pure cyclohexenyl nucleoside building blocks for oligonucleotide synthesis" Tetrahedron (2004) 60(9): 2111-2123.

Hegele et al., "A polygenic basis for four classical Fredrickson hyperlipoproteinemia phenotypes that are characterized by hypertriglyceridemia." Human Molecular Genetics (2009) 18:4189-4194.

Hegele et al., "Hypertriglyceridemia: phenomics and genomics." Mol. Cell. Biochem. (2009) 326:35-43.

Horvath et al., "Stereoselective synthesis of (-)-ara-cyclohexenyl-adenine" Tetrahedron Letters (2007) 48: 3621-3623.

International Search Report and Written Opinion from PCT/US04/10946 dated Feb. 22, 2006.

International Search Report from application PCT/US2012/035694 dated Jul. 19, 2012.

International Search Report from application PCT/US2014/043723 dated Feb. 6, 2016.

Jama, "Executive summary of the third report of the National Cholesterol Education Program (NCEP) expert panel on detection, evaluation, and treatment of high blood cholesterol in adults (adult treatment panel III)" (2001) 285:2486-2497.

Klein et al., "P284: Apoprotein C-III (ApoCIII) Protein Concentrations and Gene Polymorphisms in Type 1 Diabetes" Aretioscler. Thromb. Vase. Biol. (2002) 22(5):A-50.

Koshkin et al., "LNA (Locked Nucleic Acids): Synthesis of the Adenine, Cytosine, Guanine, 5-Methylcytosine, Thymine and Ura-

(56) References Cited

OTHER PUBLICATIONS cil Bicyclonucleoside Monomers, Oligomerisation, and Unprecedented Nucleic Acid Recognition" Tetrahedron (1998) 54: 3607-3630.
Kumar et al., "The first analogues of LNA (locked nucleic acids): phosphorothioate-LNA and 2'-thio-LNA." Bioorg. Med. Chem. Lett. (1998) 8: 2219-2222.
Lee et al., "Apolipoprotein CIII overexpressing mice are predisposed to diet-induced hepatic steatosis and hepatic insulin resistance" Hepatology (2011) 54:1650-1660.
Lee et al., "LDL containing apolipoprotein CIII is an independent risk factor for coronary events in diabetic patients" Arterioscler Thromb Vasc Biol. (2003) 23:853-858.
Leumann et al., "DNA Analogues: From Supramolecular Principles to Biological Properties" Bioorganic & Medicinal Chemistry (2002) 10:841-854.
Li et al., "Common genetic variation in the promoter of the human apo CIII gene abolishes regulation by insulin and may contribute to hypertriglyceridemia" J. Clin. Invest. (1995) 96:2601-2605.
Maher et al., "Comparative hybrid arrest by tandem antisense oligodeoxyribonucleotides or oligodeoxyribonucleoside methylphosphonates in a cell-free system" Nuc. Acid. Res. (1988) 16(8):3341-3358.
Martin, "Ein newer Zugang zu 2'-O-Alkylribonucleosiden and Eigenscbaften deren Oligonucleotide" Helv. Chim. Acta (1995)78: 486-504.
Mauger et al., "Apolipoprotein C-III isoforms: kinetics and relative implication in lipid metabolism" Journal of Lipid Research (2006) 47:1212-1218.
Mendivil et al., "Low-density lipoproteins containing apolipoprotein C-III and the risk of coronary heart disease." Circulation (2011) 124:2065-2072.
Nauwelaerts et al., "Cyclohexenyl nucleic acids: conformationally flexible oligonucleotides" Nucleic Acids Research (2005) 33(8): 2452-2463.
Nauwelaerts et al., "Structural Characterization and Biological Evaluation of Small Interfering RNAs Containing Cyclohexenyl Nucleosides" J. Am. Chem. Soc. (2007) 129(30): 9340-9348.
NCEP "Third report of the National Cholesterol Education Program (NCEP Expert Panel on detection, evaluation, and treatment of high blood cholesterol in adults (Adult Treatment Panel III) Final Report" (2002) Circulation 106:3143-421.
Olivieri et al., "Apolipoprotein C-III, n-3 Polyunsaturated Fatty Acids, and "Insulin-Resistant" T-455C APOC3 Gene Polymorphism in Heart Disease Patients: Example of Gene-Diet Interaction" Clin. Chem. (2005) 51(2):360-367.
Ooi et al., "Apolipoprotein C-III: understanding an emerging cardiovascular risk factor." Clinical Science London (2008) 114: 611-624.
Orum et al., "Locked nucleic acids: A promising molecular family for gene-function analysis and antisense drug development" Curr. Opinion Mol. Ther. (2001) 3: 239-243.
Petersen et al., "Apolipoprotein C3 Gene Variants in Nonalcoholic Fatty Liver Disease" The New England Journal of Medicine (2010) 362(12):1082-1089.
Reaven et al., "Hypertriglyceridemic mice transgenic for human apolipoprotein C-III gene are neither insulin resistant nor hyperinsulinemic" Journal of Lipid Res. (1994) 35:820-824.
Robeyns et al., "Oligonucleotides with cyclohexene-nucleoside building blocks: crystallization and preliminary X-ray studies of a left-handed sequence GTGT ACAC" Acta Crystallographica, Section F: Structural Biology and Crystallization Communications (2005) F61(6): 585-586.
Robeyns et al., "Structure of the Fully Modified Left-Handed Cyclohexene Nucleic Acid Sequence GTGTACAC" J. Am. Chem. Soc. (2008) 130(6): 1979-1984.
Sacks et al., "VLDL, apolopoproteins B, CIII, and E, and risk of recurrent coronary events in the Cholesterol and Recurrent Events (CARE) trial." Circulation (2000) 102:1886-1892.
Samuel et al., "Mechanisms for insulin resistance: common threads and missing links." Cell (2012) 148(5):852-871.
Schachter "Apolipoproteins C-I and C-III as important modulators of lipoprotein metabolism" Curr. Opin. Lipidol. (2001) 12:297-304.
Singh et al., "LNA (locked nucleic acids): synthesis and high-affinity nucleic acid recognition" Chem. Commun. (1998) 4: 455-456.
Singh et al., "Synthesis of 2'-Amino-LNA: A Novel Conformationally Restricted High-Affinity Oligonucleotide Analogue with a Handle" J. Org. Chem. (1998) 63: 10035-10039.
Srivastava et al., "Five- and Six-Membered Conformationally Locked 2', 4'-Carbocyclic ribo-Thymidines: Synthesis, Structure, and Biochemical Studies" J. Am. Chem. Soc. (2007) 129(26): 8362-8379.
Steele, "Influences of glucose loading and of injected insulin on hepatic glucose output" Annals of the New York Academy of Science (1959) 82:420-430.
Supplementary European Search Report for EP 04749914.0 dated Jan. 5, 2009.
Toskes, "Hyperlipidemic Pancreatitis" Disorders of the Pancreas (1990) 19:783-791.
Verbeure et al., "RNase H mediated cleavage of RNA by cyclohexene nucleic acid (CeNA)" Nucleic Acids Research (2001) 29(24): 4941-4947.
Wahlestedt et al., "Potent and nontoxic antisense oligonucleotides containing locked nucleic acids" PNAS (2000) 97: 5633-5638.
Wang et al., "A Straightforward Stereoselective Synthesis of D- and L-5-Hydroxy-4-hydroxymethyl-2-cyclohexenylguanine" J. Org. Chem. (2001) 66: 8478-8482.
Wang et al., "Cyclohexene nucleic acids (CeNA) form spable duplexes with RNA and induce RNAS H Activity" Nucleosides, Nucleotides & Nucleic Acids (2001) 20(4-7) 785-788.
Wang et al., "Cyclohexene Nucleic Acids (CeNA): Serum Stable Oligonucleotides that Activate RNase H and Increase Duplex Stability with Complementary RNA" J. Am. Chem. (2000) 122: 8595-8602.
Wang et al., "Stereocontrolled Synthesis of Ara-Type Cyclohexenyl Nucleosides" J. Org. Chem. (2003) 68: 4499-4505.
Weissglas-Volkov et al., Genetic causes of high and low serum HDL-cholesterol. Journal of Lipid Research (2010) 51:2032-2057.
Woolf et al. "Specificity of antisense oligonucleotides in vivo" PNAS (1992) 89:7305-7309.
Zhang et al., "PowerBLAST: A New Network BLAST Application for Interactive or Automated Sequence Analysis and Annotation" Genome Res. (1997) 7:649-656.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

\* cited by examiner

SEQUENCE LISTING

<160> NUMBER OF SEQ ID NOS: 4

<210> SEQ ID NO 1
<211> LENGTH: 533
<212> TYPE: DNA
<213> ORGANISM: Homo sapiens

<400> SEQUENCE: 1

```
tgctcagttc atccctagag gcagctgctc caggaacaga ggtgccatgc agccccgggt      60
actccttgtt gttgccctcc tggcgctcct ggcctctgcc cgagcttcag aggccgagga     120
tgcctccctt ctcagcttca tgcagggtta catgaagcac gccaccaaga ccgccaagga     180
tgcactgagc agcgtgcagg agtcccaggt ggcccagcag gccaggggct gggtgaccga     240
tggcttcagt tccctgaaag actactggag caccgttaag gacaagttct ctgagttctg     300
ggatttggac cctgaggtca gaccaacttc agccgtggct gcctgagacc tcaataccc      360
aagtccacct gcctatccat cctgcgagct ccttgggtcc tgcaatctcc agggctgccc     420
ctgtaggttg cttaaaaggg acagtattct cagtgctctc ctaccccacc tcatgcctgg     480
ccccctcca ggcatgctgg cctcccaata aagctggaca agaagctgct atg             533
```

<210> SEQ ID NO 2
<211> LENGTH: 3964
<212> TYPE: DNA
<213> ORGANISM: Homo sapiens

<400> SEQUENCE: 2

```
ctactccagg ctgtgttcag ggcttggggc tggtggaggg aggggcctga aattccagtg      60
tgaaaggctg agatgggccc gaggcccctg gcctatgtcc aagccatttc ccctctcacc     120
agcctctccc tggggagcca gtcagctagg aaggaatgag ggctccccag gcccaccccc     180
agttcctgag ctcatctggg ctgcaggggct ggcgggacag cagcgtggac tcagtctcct    240
agggatttcc caactctccc gcccgcttgc tgcatctgga caccctgcct caggccctca     300
tctccactgg tcagcaggtg acctttgccc agcgccctgg gtcctcagtg cctgctgccc     360
tggagatgat ataaaacagg tcagaaccct cctgcctgtc tgctcagttc atccctagag     420
gcagctgctc caggtaatgc cctctgggga ggggaaagag gaggggagga ggatgaagag     480
gggcaagagg agctccctgc ccagcccagc cagcaagcct ggagaagcac ttgctagagc     540
taaggaagcc tcggagctgg acgggtgccc ccaccctc atcataacct gaagaacatg       600
gaggcccggg aggggtgtca cttgcccaaa gctacacagg gggtgggggct ggaagtggct    660
ccaagtgcag gttccccccct cattcttcag gcttagggct ggaggaagcc ttagacagcc    720
cagtcctacc ccagacaggg aaactgaggc ctggagaggg ccagaaatca cccaaagaca     780
cacagcatgt tggctggact ggacggagat cagtccagac cgcaggtgcc ttgatgttca     840
gtctggtggg ttttctgctc catcccaccc acctcccttt gggcctcgat ccctcgcccc     900
tcaccagtcc cccttctgag agcccgtatt agcagggagc cggcccctac tccttctggc     960
agacccagct aaggttctac cttaggggcc acgccacctc cccagggagg ggtccagagg    1020
catggggacc tggggtgccc ctcacaggac acttccttgc aggaacagag gtgccatgca    1080
gccccgggta ctccttgttg ttgccctcct ggcgctcctg gcctctgccc gtaagcactt    1140
ggtgggactg ggctgggggc agggtggagg caacttgggg atcccagtcc caatgggtgg    1200
tcaagcagga gccagggct cgtccagagg ccgatccacc ccactcagcc ctgctctttc     1260
ctcaggagct tcagaggccg aggatgcctc ccttctcagc ttcatgcagg ttacatgaa      1320
gcacgccacc aagaccgcca aggatgcact gagcagcgtg caggagtccc aggtggccca    1380
gcaggccagg tacacccgct ggcctccctc cccatccccc ctgccagctg cctccattcc    1440
cacccgcccc tgccctggtg agatcccaac aatggaatgg aggtgctcca gcctcccctg    1500
ggcctgtgcc tcttcagcct cctctttcct cacagggcct tgtcaggct gctgcgggag      1560
agatgacaga gttgagactg cattcctccc aggtccctcc tttctccccg gagcagtcct    1620
agggcgtgcc gttttagccc tcatttccat tttcctttcc tttcccttc tttctcttc       1680
tatttctttc tttctttctt tctttctttc tttctttctt tctttctttc tttctttctt    1740
tctttctttc ctttctttct ttcctttctt tctttccttt ctttctttct ttcctttctt    1800
tctcttcttt tctttctttc cttttctttt cttcccctct cttcctttct ctctttcttt    1860
cttcttcttt tttttttaat ggagtctccc tctgtcacct aggctggagt gcagtggtgc    1920
catctcggct cactgcaacc tccgtctccc gggttcaacc cattctcctg cctcagcctc    1980
ccaagtagct gggattacag gcacgcgcca ccacacccag ctaattttg tattttagc       2040
agagatgggg tttcaccatg ttggccaggt tggtcttgaa ttcctgacct cagggatcc       2100
tcctgcctcg gcctcccaaa gtgctgggat tacaggcatg agccactgcg cctggcccca    2160
```

| | |
|---|---|
| tttccttttt ctgaaggtct ggctagagca gtggtcctca gccttttggg caccagggac | 2220 |
| cagttttgtg gtggacaatt tttccatggg ccagcgggga tggttttggg atgaagctgt | 2280 |
| tccacctcag atcatcaggc attagattct cataaggagc cctccaccta gatccctggc | 2340 |
| atgtgcagtt cacaataggg ttcacactcc tatgagaatg taaggccact tgatctgaca | 2400 |
| ggaggcggag ctcaggcggt attgctcact cacccaccac tcacttcgtg ctgtgcagcc | 2460 |
| cggctcctaa cagtccatgg accagtacct atctatgact tgggggttgg ggaccccctgg | 2520 |
| gctaggggtt tgccttggga ggccccacct gacccaattc aagcccgtga gtgcttctgc | 2580 |
| tttgttctaa gacctggggc cagtgtgagc agaagtgtgt ccttcctctc ccatcctgcc | 2640 |
| cctgcccatc agtactctcc tctcccctac tcccttctcc acctcaccct gactggcatt | 2700 |
| agctggcata gcagaggtgt tcataaacat tcttagtccc cagaaccggc tttgggtag | 2760 |
| gtgttatttt ctcactttgc agatgagaaa attgaggctc agagcgatta ggtgacctgc | 2820 |
| cccagatcac acaactaatc aatcctccaa tgactttcca aatgagaggc tgcctccctc | 2880 |
| tgtcctaccc tgctcagagc caccaggttg tgcaactcca ggcggtgctg tttgcacaga | 2940 |
| aaacaatgac agccttgacc tttcacatct ccccaccctg tcactttgtg cctcaggccc | 3000 |
| aggggcataa acatctgagg tgacctggag atggcagggt ttgacttgtg ctggggttcc | 3060 |
| tgcaaggata tctcttctcc cagggtggca gctgtggggg attcctgcct gaggtctcag | 3120 |
| ggctgtcgtc cagtgaagtt gagagggtgg tgtggtcctg actggtgtcg tccagtgggg | 3180 |
| acatgggtgt gggtcccatg gttgcctaca gaggagttct catgccctgc tctgttgctt | 3240 |
| cccctgactg atttaggggc tgggtgaccg atggcttcag ttccctgaaa gactactgga | 3300 |
| gcaccgttaa ggacaagttc tctgagttct gggatttgga ccctgaggtc agaccaactt | 3360 |
| cagccgtggc tgcctgagac ctcaataccc caagtccacc tgcctatcca tcctgcgagc | 3420 |
| tccttgggtc ctgcaatctc cagggctgcc cctgtaggtt gcttaaaagg gacagtattc | 3480 |
| tcagtgctct cctaccccac ctcatgcctg gcccccctcc aggcatgctg gcctcccaat | 3540 |
| aaagctggac aagaagctgc tatgagtggg ccgtcgcaag tgtgccatct gtgtctgggc | 3600 |
| atgggaaagg gccgaggctg ttctgtgggt gggcactgga cagactccag gtcaggcagg | 3660 |
| catggaggcc agcgctctat ccaccttctg gtagctgggc agtctctggg cctcagtttc | 3720 |
| ttcatctcta aggtaggaat cacccctccgt accctgcctt ccttgacagc tttgtgcgga | 3780 |
| aggtcaaaca ggacaataag tttgctgata cttttgataaa ctgttaggtg ctgcacaaca | 3840 |
| tgacttgagt gtgtgcccca tgccagccac tatgcctggc acttaagttg tcatcagagt | 3900 |
| tgagactgtg tgtgtttact caaaactgtg gagctgacct cccctatcca ggccccctag | 3960 |
| ccct | 3964 |

<210> SEQ ID NO 3
<211> LENGTH: 3958
<212> TYPE: DNA
<213> ORGANISM: Homo sapiens

<400> SEQUENCE: 3

| | |
|---|---|
| ctactccagg ctgtgttcag ggcttggggc tggtggaggg aggggcctga aattccagtg | 60 |
| tgaaaggctg agatgggccc gaggcccctg gcctatgtcc aagccatttc ccctctcacc | 120 |
| agcctctccc tggggagcca gtcagctagg aaggaatgag ggctccccag gcccaccccc | 180 |
| agttcctgag ctcatctggg ctgcagggct ggcgggacag cagcgtggac tcagtctcct | 240 |

```
agggatttcc caactctccc gcccgcttgc tgcatctgga caccctgcct caggccctca    300
tctccactgg tcagcaggtg acctttgccc agcgccctgg gtcctcagtg cctgctgccc    360
tggagatgat ataaaacagg tcagaaccct cctgcctgtc tgctcagttc atccctagag    420
gcagctgctc caggtaatgc cctctgggga ggggaaagag gagggagga ggatgaagag     480 gggcaagagg agctccctgc ccagcccagc cagcaagcct ggagaagcac ttgctagagc    540
taaggaagcc tcggagctgg acgggtgccc cccaccctc atcataacct gaagaacatg     600
gaggcccggg aggggtgtca cttgcccaaa gctacatagg gggtggggct ggaagtggct    660
ccaagtgcag gttcccccct cattcttcag gcttagggct ggaggaagcc ttagacagcc    720
cagtcctacc ccagacaggg aaactgaggc ctggagaggg ccagaaatca cccaaagaca    780
cacagcatgt tggctggact ggacggagat cagtccagac cgcaggtgcc ttgatgttca    840
gtctggtggg ttttctgctc catcccaccc acctcccttt gggcctcgat ccctcgcccc    900
tcaccagtcc cccttctgag agcccgtatt agcaggagc cggccctac tccttctggc      960 agacccagct aaggttctac cttaggggcc acgccacctc cccagggagg ggtccagagg   1020
catggggacc tggggtgccc ctcacaggac acttccttgc aggaacagag gtgccatgca   1080
gccccgggta ctccttgttg ttgccctcct ggcgctcctg gcctctgccc gtaagcactt   1140
ggtgggactg ggctggggc agggtggagg caacttgggg atcccagtcc caatgggtgg    1200
tcaagcagga gcccagggct cgtccatagg ccgatccacc ccactcagcc ctgctctttc   1260
ctcaggagct tcagaggccg aggatgcctc ccttctcagc ttcatgcagg gctacatgaa   1320
gcacgccacc aagaccgcca aggatgcact gagcagcgtg caggagtccc aggtggccca   1380
gcaggccagg tacacccgct ggcctccctc cccatccccc ctgccagctg cctccattcc   1440
cacccacccc tgccctggtg agatcccaac aatggaatgg aggtgctcca gcctcccctg   1500
ggcctgtgcc tcttcagcct cctctttcct cacagggcct ttgtcaggct gctgcgggag   1560
agatgacaga gttgagactg cattcctccc aggtccctcc tttctcccca gagcagtcct   1620
agggcgcgcc gttttagccc tcatttccat tttccttcc tttccctttc tttcccttc     1680 tatttctttc tttctttctt tcttctttc tttcttct tctttcttc tttctttctt       1740 tctttcttc ctttctttct ttcttttctt ctttctttct ttcctttctt tctcttctt     1800 tcttcttc tttcctttt ctttctttcc ctctcttcct ttctctcttt ctttcttctt      1860
cttttttttt taatggagtc tccctctgtc acccaggctg gagtgcagtg gtgccatctc   1920
ggctcactgc aacctccgtc tcccgggttc aacccattct cctgcctcag cctcccaagt   1980
agctgggatt acaggcacgc gccaccacac ccagctaatt tttgtatttt tagcagagat   2040
ggggtttcac catgttggcc aggttggtct tgaattcctg acctcagggg atcctcctgc   2100
ctcggcctcc caaagcgctg ggattacagg catgagccac tgcgcctggc cccattttcc   2160
ttttctgaag gtctggctag agcagtggtc ctcagccttt ttggcaccag gaccagttt    2220 tgtggtggac aattttttcca tgggccagcg gggatggttt tgggatgaag ctgttccacc   2280
tcagatcatc aggcattaga ttctcataag gagccctcca cctagatccc tggcatgtgc    2340
agttcacaac agggttcaca ctcctatgag aatgtaaggc cacttgatct gacaggaggc   2400
ggagctcagg cggtattgct cactcaccca ccactcactt cgtgctgtgc agcccggctc   2460
ctaacagtcc atggaccagt acctatctat gacttgggg ttgggaccc ctgggctagg      2520 ggtttgcctt gggaggcccc acctgaccta attcaagccc gtgagtgctt ctgctttgtt    2580
ctaagacctg gggccagtgt gagcagaagt gtgtccttcc tctcccatcc tgcccctgcc    2640
```

```
catcagtact ctcctctccc ctactccctt ctccacctca ccctgactgg cattagctgg      2700
catagcagag gtgttcataa acattcttag tccccagaac cggctttggg gtaggtgtta      2760
ttttctcact ttgcagatga gaaaattgag gctcagagcg attaggtgac ctgccccaga      2820
tcacacaact aatcaatcct ccaatgactt tccaaatgag aggctgcctc cctctgtcct      2880
accctgctca gagccaccag gttgtgcaac tccaggcggt gctgtttgca cagaaaacaa      2940
tgacagcctt gacctttcac atctccccac cctgtcactt tgtgcctcag gcccaggggc      3000
ataaacatct gaggtgacct ggagatggca gggtttgact tgtgctgggg ttcctgcaag      3060
gatatctctt ctcccagggt ggcagctgtg ggggattcct gcctgaggtc tcagggctgt      3120
cgtccagtga agttgagagg gtggtgtggt cctgactggt gtcgtccagt ggggacatgg      3180
gtgtgggtcc catggttgcc tacagaggag ttctcatgcc ctgctctgtt gcttccctg       3240 actgatttag gggctgggtg accgatggct tcagttccct gaaagactac tggagcaccg      3300
ttaaggacaa gttctctgag ttctgggatt tggaccctga ggtcagacca acttcagccg      3360
tggctgcctg agacctcaat accccaagtc cacctgccta tccatcctgc cagctccttg      3420
ggtcctgcaa tctccagggc tgcccctgta ggttgcttaa aagggacagt attctcagtg      3480
ctctcctacc ccacctcatg cctggccccc tccaggcat gctggcctcc caataaagct       3540
ggacaagaag ctgctatgag tgggccgtcg caagtgtgcc atctgtgtct gggcatggga      3600
aagggccgag gctgttctgt gggtgggcac tggacagact ccaggtcagg caggcatgga      3660
ggccagcgct ctatccacct tctggtagct gggcagtctc tgggcctcag tttcttcatc      3720
tctaaggtag gaatcaccct ccgtaccctg ccttccttga cagctttgtg cggaaggtca      3780
aacaggacaa taagtttgct gatactttga taaactgtta ggtgctgcac aacatgactt      3840
gagtgtgtgc cccatgccag ccactatgcc tggcacttaa gttgtcatca gagttgagac      3900
tgtgtgtgtt tactcaaaac tgtggagctg acctccccta tccaggccac ctagccct       3958
```

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4

```
agcttcttgt ccagctttat                                                    20
```

COMPOUNDS AND METHODS FOR MODULATING APOLIPOPROTEIN C-III EXPRESSION FOR IMPROVING A DIABETIC PROFILE

SEQUENCE LISTING

The present application is being filed along with a Sequence Listing in electronic format. The Sequence Listing is provided as a file entitled BIOL0225WOSEQ_ST25.txt, created on Jun. 20, 2014 which is 12 Kb in size. The information in the electronic format of the sequence listing is incorporated herein by reference in its entirety.

The present application is being filed along with a Sequence Listing in electronic format. The Sequence Listing is provided as a file entitled BIOL0225USASEQ_ST25.txt, created on Dec. 18, 2015 which is 12 Kb in size. The information in the electronic format of the sequence listing is incorporated herein by reference in its entirety.

FIELD OF THE INVENTION

Provided herein are improved compounds, compositions and associated methods for reducing expression of Apolipoprotein C-III (ApoCIII) mRNA and protein in a diabetic subject or a subject at risk for diabetes.

BACKGROUND

Apolipoprotein C-III (also called APOC3, APOC-III, ApoCIII, and APO C-III) is a constituent of HDL and of triglyceride (TG)-rich lipoproteins. ApoCIII slows clearance of TG-rich lipoproteins by inhibiting lipolysis through inhibition of lipoprotein lipase (LPL) and through interfering with lipoprotein binding to cell-surface glycosaminoglycan matrix (Shachter, *Curr. Opin. Lipidol*, 2001, 12, 297-304).

Elevated ApoCIII levels have been associated with elevated TG levels, elevated hepatic insulin resistance and diseases such as cardiovascular disease, metabolic syndrome, non-alcoholic fatty liver disease (NAFLD), obesity and diabetes (Chan et al., *Int J Clin Pract*, 2008, 62:799-809; Onat et al., Atherosclerosis, 2003, 168:81-89; Mendivil et al., *Circulation*, 2011, 124:2065-2072; Mauger et al., *J. Lipid Res*, 2006, 47: 1212-1218; Chan et al., *Clin. Chem*, 2002. 278-283; Ooi et al., *Clin. Sci*, 2008, 114: 611-624; Davidsson et al., *J. Lipid Res.* 2005, 46: 1999-2006; Sacks et al., *Circulation*, 2000, 102: 1886-1892; Lee et al., *Arterioscler Thromb Vasc Biol*, 2003. 23: 853-858; Lee et al., *Hepatology*, 2011, 54:1650-1660) while a null mutation in human ApoCIII was found to confer a favorable plasma lipid profile and cardioprotection (Pollin et al., *Science*, 2008, 322:1702-1705) leading to the assumption that decreasing ApoCIII levels would ameliorate certain diseases associated with elevated ApoCIII or improve physiological markers of disease such as insulin resistance.

However, the relationship between ApoCIII and disease is complicated. For example, some studies have suggested that decreasing ApoCIII levels would not necessarily improve insulin resistance in a subject. Hypertriglyceridemic mice transgenic for the human ApoCIII gene were not found to be insulin resistant (Reaven et al., *J. Lipid Res*, 1994, 35:820-824). However, a different study in ApoCIII transgenic mice found severe hepatic insulin resistance but no peripheral insulin resistance change (Lee et al., *Arterioscler Thromb Vasc Biol*, 2003. 23: 853-858; Lee et al., *Hepatology*, 2011, 54:1650-1660). Further, in a mouse ApoCIII knockout model, obesity and insulin resistance was increased (Duivenvoorden et al., *Diabetes,* 2005, 54:664-671). Accordingly, further study is needed to determine whether the effects of decreasing ApoCIII levels would ameliorate diseases associated with elevated ApoCIII such as diabetes, or the risk of diabetes, or improve physiological markers of disease such as insulin resistance Antisense technology is emerging as an effective means for reducing the expression of certain gene products and may prove to be uniquely useful in a number of therapeutic, diagnostic, and research applications for the modulation of ApoCIII. Antisense compounds targeting ApoCIII and associated methods for inhibiting ApoCIII have been previously disclosed (see e.g., U.S. Pat. No. 7,598,227, U.S. Pat. No. 7,750,141, PCT publication WO 2004/093783 and PCT publication WO 2012/149495, all incorporated-by-reference herein). An antisense compound targeting ApoCIII, ISIS-APOCIII$_{Rx}$, has been tested in a Phase I clinical trial and was shown to be safe. Currently, ISIS-APOCIII$_{Rx}$ is in Phase II clinical trials to assess its effectiveness in the treatment of hypertriglyceridemia. However, there is still a need to provide additional and more potent treatment options for subjects having, or have a risk for, diabetes.

SUMMARY OF THE INVENTION

Certain embodiments provide a method of improving insulin sensitivity comprising, selecting a subject with diabetes and administering a compound comprising an antisense oligonucleotide 12-30 nucleobases in length targeting ApoCIII thereby improving insulin sensitivity. In certain embodiments, the insulin sensitivity is peripheral insulin sensitivity. In certain embodiments, the subject has type II diabetes. In certain embodiments, the subject has moderately controlled type II diabetes.

Certain embodiments provide a method of lowering free fatty acids comprising, selecting a subject with diabetes and administering a compound comprising an antisense oligonucleotide 12-30 nucleobases in length targeting ApoCIII, thereby lowering free fatty acids. In certain embodiments, the subject has type II diabetes. In certain embodiments, the subject has moderately controlled type II diabetes.

Certain embodiments provide a method of reducing intramyocellular triglyceride deposition comprising, selecting a subject with diabetes and administering a compound comprising an antisense oligonucleotide 12-30 nucleobases in length targeting ApoCIII, thereby reducing intramyocellular triglyceride deposition. In certain embodiments, the subject has type II diabetes. In certain embodiments, the subject has moderately controlled type II diabetes.

Certain embodiments provide a method of improving a lipid profile of a subject comprising, administering a compound comprising an antisense oligonucleotide 12-30 nucleobases in length targeting ApoCIII, wherein free fatty acids, triglycerides, non-HDL-C, VLDL-C, ApoCIII containing VLDL, ApoB and LDL-C are reduced and HDL-C is increased, thereby improving the lipid profile of the subject.

Certain embodiments provide a method of improving a diabetes profile of a subject comprising administering a compound comprising an antisense oligonucleotide 12-30 nucleobases in length targeting ApoCIII, wherein insulin sensitivity index, glucose disposal rate, glucose MCR, glucose metabolism:insulin ration is improved; wherein free fatty acids, intramyocellular triglyceride deposition, triglycerides, non-HDL-C, VLDL-C, ApoCIII containing VLDL, ApoB and LDL-C are reduced and HDL-C is increased, thereby improving the diabetes profile of the subject.

In certain embodiments, the subject is on a stable dose of metformin.

In certain embodiments, the subject has fasting triglyceride levels≥200 and ≤500 mg/dl.

In certain embodiments, the antisense oligonucleotide has a sequence complementary to any of the sequences set forth in GENBANK Accession No. NM_000040.1 (incorporated herein as SEQ ID NO: 1), GENBANK Accession No. NT_033899.8 truncated from nucleotides 20262640 to 20266603 (incorporated herein as SEQ ID NO: 2), and GenBank Accession No. NT_035088.1 truncated from nucleotides 6238608 to U.S. Pat. No. 6,242,565 (incorporated herein as SEQ ID NO: 3). In certain embodiments, the antisense oligonucleotide is at least 70%, at least 75%, at least 80%, at least 85%, at least 90%, at least 95%, at least 98% or at least 100% complementary to SEQ ID NO: 1, SEQ ID NO: 2 or SEQ ID NO: 3.

In certain embodiments, the antisense oligonucleotide comprises at least 8 nucleobases of the sequence of SEQ ID NO: 4. In certain embodiments, the antisense oligonucleotide comprises the sequence of SEQ ID NO: 4. In certain embodiments, the antisense oligonucleotide consists of the sequence of SEQ ID NO: 4.

In certain embodiments, the antisense oligonucleotide has a nucleobase sequence comprising at least 8 contiguous nucleobases of a sequence selected from any sequence disclosed in U.S. Pat. No. 7,598,227, U.S. Pat. No. 7,750,141, PCT Publication WO 2004/093783 or PCT Publication WO 2012/149495, all incorporated-by-reference herein. In certain embodiments, the antisense oligonucleotide has a sequence selected from any sequence disclosed in U.S. Pat. No. 7,598,227, U.S. Pat. No. 7,750,141, PCT Publication WO 2004/093783 or PCT Publication WO 2012/149495, all incorporated-by-reference herein.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings

"2'-O-methoxyethyl" (also 2'-MOE, 2'-O(CH$_2$)$_2$—OCH$_3$ and 2'-O-(2-methoxyethyl)) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5 position. A 5-methylcytosine is a modified nucleobase.

"About" means within ±10% of a value. For example, if it is stated, "a marker may be increased by about 50%", it is implied that the marker may be increased between 45%-55%.

"Active pharmaceutical agent" means the substance or substances in a pharmaceutical composition that provide a therapeutic benefit when administered to an individual. For example, in certain embodiments an antisense oligonucleotide targeted to ApoCIII is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the subject at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Agent" means an active substance that can provide a therapeutic benefit when administered to an animal. "First Agent" means a therapeutic compound of the invention. For example, a first agent can be an antisense oligonucleotide targeting ApoCIII. "Second agent" means a second therapeutic compound of the invention (e.g. a second antisense oligonucleotide targeting ApoCIII) and/or a non-ApoCIII targeting therapeutic compound.

"Amelioration" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAi and occupancy-based compounds.

"Antisense inhibition" means the reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid. As used herein, the term "antisense oligonucleotide" encompasses pharmaceutically acceptable derivatives of the compounds described herein.

"ApoCIII", "Apolipoprotein C-III" or "ApoC3" means any nucleic acid or protein sequence encoding ApoCIII. For example, in certain embodiments, an ApoCIII includes a DNA sequence encoding ApoCIII, a RNA sequence transcribed from DNA encoding ApoCIII (including genomic DNA comprising introns and exons), a mRNA sequence encoding ApoCIII, or a peptide sequence encoding ApoCIII.

"ApoCIII specific inhibitor" refers to any agent capable of specifically inhibiting the expression of ApoCIII mRNA and/or the expression or activity of ApoCIII protein at the molecular level. For example, ApoCIII specific inhibitors include nucleic acids (including antisense compounds), peptides, antibodies, small molecules, and other agents capable of inhibiting the expression of ApoCIII mRNA and/or ApoCIII protein. In certain embodiments, the nucleic acid is an antisense compound. In certain embodiments, the antisense compound is a an oligonucleotide targeting ApoCIII. In certain embodiments, the oligonucleotide targeting ApoCIII is a modified oligonucleotide targeting ApoCIII. In certain embodiments, the oligonucleotide targeting ApoCIII has a sequence as shown in SEQ ID NO: 4 or another sequence, for example, such as those disclosed in U.S. Pat. No. 7,598,227, U.S. Pat. No. 7,750,141, PCT Publication WO 2004/093783 or PCT Publication WO 2012/149495, all incorporated-by-reference herein. In certain embodiments, by specifically modulating ApoCIII mRNA level and/or ApoCIII protein expression, ApoCIII specific inhibitors may affect components of the lipogenic or glucogenic pathway. Similarly, in certain embodiments, ApoCIII specific inhibitors may affect other molecular processes in an animal.

"ApoCIII mRNA" means a mRNA encoding an ApoCIII protein.

"ApoCIII protein" means any protein sequence encoding ApoCIII.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Cardiovascular disease" or "cardiovascular disorder" refers to a group of conditions related to the heart, blood vessels, or the circulation. Examples of cardiovascular diseases include, but are not limited to, aneurysm, angina, arrhythmia, atherosclerosis, cerebrovascular disease (stroke), coronary heart disease, hypertension, dyslipidemia, hyperlipidemia, hypertriglyceridemia and hypercholesterolemia.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Cholesterol" is a sterol molecule found in the cell membranes of all animal tissues. Cholesterol must be transported in an animal's blood plasma by lipoproteins including very low density lipoprotein (VLDL), intermediate density lipoprotein (IDL), low density lipoprotein (LDL), and high density lipoprotein (HDL). "Plasma cholesterol" refers to the sum of all lipoproteins (VDL, IDL, LDL, HDL) esterified and/or non-esterified cholesterol present in the plasma or serum.

"Cholesterol absorption inhibitor" means an agent that inhibits the absorption of exogenous cholesterol obtained from diet.

"Co-administration" means administration of two or more agents to an individual. The two or more agents can be in a single pharmaceutical composition, or can be in separate pharmaceutical compositions. Each of the two or more agents can be administered through the same or different routes of administration. Co-administration encompasses parallel or sequential administration.

"Complementarity" means the capacity for pairing between nucleobases of a first nucleic acid and a second nucleic acid. In certain embodiments, complementarity between the first and second nucleic acid can be between two DNA strands, between two RNA strands, or between a DNA and an RNA strand. In certain embodiments, some of the nucleobases on one strand are matched to a complementary hydrogen bonding base on the other strand. In certain embodiments, all of the nucleobases on one strand are matched to a complementary hydrogen bonding base on the other strand. In certain embodiments, a first nucleic acid is an antisense compound and a second nucleic acid is a target nucleic acid. In certain such embodiments, an antisense oligonucleotide is a first nucleic acid and a target nucleic acid is a second nucleic acid.

"Contiguous nucleobases" means nucleobases immediately adjacent to each other.

"Constrained ethyl" or "cEt" refers to a bicyclic nucleoside having a furanosyl sugar that comprises a methyl (methyleneoxy) (4'-CH(CH$_3$)—O-2') bridge between the 4' and the 2' carbon atoms.

"Cross-reactive" means an oligomeric compound targeting one nucleic acid sequence can hybridize to a different nucleic acid sequence. For example, in some instances an antisense oligonucleotide targeting human ApoCIII can cross-react with a murine ApoCIII. Whether an oligomeric compound cross-reacts with a nucleic acid sequence other than its designated target depends on the degree of complementarity the compound has with the non-target nucleic acid sequence. The higher the complementarity between the oligomeric compound and the non-target nucleic acid, the more likely the oligomeric compound will cross-react with the nucleic acid.

"Cure" means a method that restores health or a prescribed treatment for an illness.

"Deoxyribonucleotide" means a nucleotide having a hydrogen at the 2' position of the sugar portion of the nucleotide. Deoxyribonucleotides may be modified with any of a variety of substituents.

"Diabetes mellitus" or "diabetes" is a group of metabolic diseases characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy. There are 3 main forms of diabetes: Type I diabetes, Type 2 diabetes and gestational diabetes. Type 1 diabetes results from the body's failure to produce insulin, and currently requires the person to inject insulin or wear an insulin pump. This form was previously referred to as "insulin-dependent diabetes mellitus" (IDDM) or "juvenile diabetes". Type 2 diabetes results from insulin resistance, a condition in which cells fail to use insulin properly, sometimes combined with an absolute insulin deficiency. This form was previously referred to as non insulin-dependent diabetes mellitus (NIDDM) or "adult-onset diabetes". The third main form, gestational diabetes occurs when pregnant women without a previous diagnosis of diabetes develop a high blood glucose level. It may precede development of type 2 diabetes. Diabetes can be measured by several parameters: percent glycated albumin, fructosamine and percent glycosylated hemoglobin levels (HbA1c). As used herein, a subject has "well controlled diabetes" or "prediabetes" if the HbA1c level is under 7%, "moderately controlled diabetes" or "moderate diabetes" if the HbA1c level is between about 7-9%, and "uncontrolled diabetes" or "severe diabetes" if the HbA1c level is greater than 9%.

"Diabetic dyslipidemia" or "type 2 diabetes with dyslipidemia" means a condition characterized by Type 2 diabetes, reduced HDL-C, elevated triglycerides, and elevated small, dense LDL particles.

"Diabetic profile" or "diabetes profile" means a summary of the diabetic state of a subject as measured by a panel of physiological markers. Physiological markers that can be assessed as part of a diabetic profile include, but are not limited to, percent glycated albumin, fructosamine levels, percent glycosylated hemoglobin (HbA1c), insulin sensitivity index, peripheral insulin sensitivity, hepatic insulin sensitivity, pancreatic insulin sensitivity, glucose disposal rate, glucose MCR, glucose metabolism:insulin ration, free fatty acids, triglycerides, non-HDL-C, VLDL-C, apoCIII containing VLDL, apoB and LDL-C; and HDL-C. An "improved diabetic profile" can include one or more of: improved insulin sensitivity index, peripheral insulin sensitivity, hepatic insulin sensitivity, pancreatic insulin sensitivity, glucose disposal rate, glucose MCR, glucose metabolism: insulin ration; lowered free fatty acids, triglycerides, non-HDL-C, VLDL-C, apoCIII containing VLDL, apoB, LDL-C, percent glycated albumin, fructosamine levels, percent glycosylated hemoglobin (HbA1c); and increased HDL.

"Diluent" means an ingredient in a composition that lacks pharmacological activity, but is pharmaceutically necessary or desirable. For example, the diluent in an injected composition may be a liquid, e.g. saline solution.

"Dyslipidemia" refers to a disorder of lipid and/or lipoprotein metabolism, including lipid and/or lipoprotein overproduction or deficiency. Dyslipidemias may be manifested by elevation of lipids such as chylomicron, cholesterol and triglycerides as well as lipoproteins such as low-density lipoprotein (LDL) cholesterol. An example of a dyslipidemia is chylomicronemia or hypertriglyceridemia.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month. Doses can also be stated as mg/kg or g/kg.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a second nucleic acid is a target nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" or "gap segment" and the external regions may be referred to as "wings" or "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Glucose" is a monosaccharide used by cells as a source of energy and inflammatory intermediate. "Plasma glucose" refers to glucose present in the plasma.

"High density lipoprotein" or "HDL" refers to a macromolecular complex of lipids (cholesterol, triglycerides and phospholipids) and proteins (apolipoproteins (apo) and enzymes). The surface of HDL contains chiefly apolipoproteins A, C and E. The function of some of these apoproteins is to direct HDL from the peripheral tissues to the liver. Serum HDL levels can be affected by underlying genetic causes (Weissglas-Volkov and Pajukanta, *J Lipid Res,* 2010, 51:2032-2057). Epidemiological studies have indicated that increased levels of HDL protect against cardiovascular disease or coronary heart disease (Gordon et al., Am. J. Med. 1977. 62: 707-714). These effects of HDL are independent of triglyceride and LDL concentrations. In clinical practice, a low plasma HDL is more commonly associated with other disorders that increase plasma triglycerides, for example, central obesity, insulin resistance, type 2 diabetes mellitus and renal disease (chronic renal failure or nephrotic proteinuria) (Kashyap. Am. J. Cardiol. 1998. 82: 42U-48U).

"High density lipoprotein-Cholesterol" or "HDL-C" means cholesterol associated with high density lipoprotein particles. Concentration of HDL-C in serum (or plasma) is typically quantified in mg/dL or nmol/L. "HDL-C" and "plasma HDL-C" mean HDL-C in serum and plasma, respectively.

"Hybridization" means the annealing of complementary nucleic acid molecules. In certain embodiments, complementary nucleic acid molecules include an antisense compound and a target nucleic acid.

"Hypercholesterolemia" means a condition characterized by elevated cholesterol or circulating (plasma) cholesterol, LDL-cholesterol and VLDL-cholesterol, as per the guidelines of the Expert Panel Report of the National Cholesterol Educational Program (NCEP) of Detection, Evaluation of Treatment of high cholesterol in adults (see, Arch. Int. Med. (1988) 148, 36-39).

"Hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins, chylomicrons and triglycerides. The Fredrickson classification of hyperlipidemias is based on the pattern of TG and cholesterol-rich lipoprotein particles, as measured by electrophoresis or ultracentrifugation and is commonly used to characterize primary causes of hyperlipidemias such as hypertriglyceridemia (Fredrickson and Lee, Circulation, 1965, 31:321-327; Fredrickson et al., New Eng J Med, 1967, 276 (1): 34-42).

"Hypertriglyceridemia" means a condition characterized by elevated triglyceride levels. Hypertriglyceridemia is the consequence of increased production and/or reduced or delayed catabolism of triglyceride (TG)-rich lipoproteins: VLDL and, to a lesser extent, chylomicrons (CM). Its etiology includes primary (i.e. genetic causes) and secondary (other underlying causes such as diabetes, metabolic syndrome/insulin resistance, obesity, physical inactivity, cigarette smoking, excess alcohol and a diet very high in carbohydrates) factors or, most often, a combination of both (Yuan et al. *CMAJ,* 2007, 176:1113-1120). Hypertriglyceridemia is a common clinical trait associated with an increased risk of cardiometabolic disease (Hegele et al. 2009, Hum Mol Genet, 18: 4189-4194; Hegele and Pollex 2009, Mol Cell Biochem, 326: 35-43) as well as of occurrence of acute pancreatitis in the most severe forms (Toskes 1990, Gastroenterol Clin North Am, 19: 783-791; Gaudet et al. 2010, Atherosclerosis Supplements, 11: 55-60; Catapano et al. 2011, Atherosclerosis, 217S: S1-S44; Tremblay et al. 2011, J Clin Lipidol, 5: 37-44). Examples of cardiometabolic disease include, but are not limited to, diabetes, metabolic syndrome/insulin resistance, and genetic disorders such as familial chylomicronemia, familial combined hyperlipidemia and familial hypertriglyceridemia. Borderline high TG levels (150-199 mg/dL) are commonly found in the general population and are a common component of the metabolic syndrome/insulin resistance states. The same is true for high TG levels (200-499 mg/dL) except that as plasma TG levels increase, underlying genetic factors play an increasingly important etiologic role. Very high TG levels (≥500 mg/dL) are most often associated with elevated CM levels as well, and are accompanied by increasing risk for acute pancreatitis. The risk of pancreatitis is considered clinically significant if TG levels exceed 880 mg/dL (>10 mmol) and the European Atherosclerosis Society/European Society of Cardiology (EAS/ESC) 2011 guidelines state that actions to prevent acute pancreatitis are mandatory (Catapano et al. 2011, Atherosclerosis, 217S: S1-S44). According to the EAS/ESC 2011 guidelines, hypertriglyceridemia is the cause of approximately 10% of all cases of pancreatitis, and development of pancreatitis can occur at TG levels between 440-880 mg/dL. Based on evidence from clinical studies demonstrating that elevated TG levels are an independent risk factor for atherosclerotic CVD, the guidelines from both the National Cholesterol Education Program Adult Treatment Panel III (NCEP 2002, Circulation, 106: 3143-421) and the American Diabetes Association (ADA 2008, Diabetes Care, 31: S12-S54.) recommend a target TG level of less than 150 mg/dL to reduce cardiovascular risk.

"Identifying" or "diagnosing" an animal with a named disease, disorder or condition means identifying, by art known methods, a subject prone to, or having, the named disease, disorder or condition. For example, identification of subjects with a disease can done by an examination of the subject's medical history in conjunction with any art known screening technique e.g., genetic screening or screening for glucose or glycosylated hemoglobin (HbA1c) levels. Identifying or diagnosing an animal with metabolic or cardiovascular disease means identifying a subject prone to, or having, a metabolic disease, a cardiovascular disease, or a metabolic syndrome; or, identifying a subject having any symptom of a metabolic disease, cardiovascular disease, or metabolic syndrome including, but not limited to, hypercholesterolemia, hyperglycemia, hyperlipidemia, hypertriglyceridemia, hypertension increased insulin resistance, decreased insulin sensitivity, above normal body weight, and/or above normal body fat content or any combination thereof. Such identification can be accomplished by any method, including but not limited to, standard clinical tests or assessments, such as measuring serum or circulating (plasma) cholesterol, measuring serum or circulating (plasma) blood-glucose, measuring serum or circulating (plasma) HbA1c, measuring serum or circulating (plasma) triglycerides, measuring blood-pressure, measuring body fat content, measuring body weight, and the like.

"Improved cardiovascular outcome" means a reduction in the occurrence of adverse cardiovascular events, or the risk thereof. Examples of adverse cardiovascular events include, without limitation, death, reinfarction, stroke, cardiogenic shock, pulmonary edema, cardiac arrest, and atrial dysrhythmia.

"Improved metabolic outcome", "improved metabolic disorder" or "improved metabolic disease" means a reduction in the occurrence of adverse metabolic events, or the risk thereof. Examples of adverse metabolic events include, without limitation, elevated glucose levels, elevated HbA1c, increased insulin resistance, decreased insulin sensitivity and increased risk or development of diabetes.

"Immediately adjacent" means there are no intervening elements between the immediately adjacent elements, for example, between regions, segments, nucleotides and/or nucleosides.

"Increasing HDL" or "raising HDL" means increasing the level of HDL in an animal after administration of at least one compound of the invention, compared to the HDL level in an animal not administered any compound.

"Individual" or "subject" or "animal" means a human or non-human animal selected for treatment or therapy.

"Induce", "inhibit", "potentiate", "elevate", "increase", "decrease", "reduce" or the like denote quantitative differences between two states. For example, "an amount effective to inhibit the activity or expression of ApoCIII" means that the level of activity or expression of ApoCIII in a treated sample will differ from the level of ApoCIII activity or expression in an untreated sample. Such terms are applied to, for example, levels of expression, and levels of activity.

"Inhibiting the expression or activity" refers to a reduction or blockade of the expression or activity of a RNA or protein and does not necessarily indicate a total elimination of expression or activity.

"Insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Insulin sensitivity" is a measure of how effectively an individual processes glucose. An individual having high insulin sensitivity effectively processes glucose whereas an individual with low insulin sensitivity does not effectively process glucose. The various types of insulin sensitivity (including, for example, "hepatic insulin sensitivity", "peripheral insulin sensitivity" and "pancreatic insulin sensitivity") refer to the tissue type wherein the insulin sensitivity occurs. Insulin sensitivity in one tissue type does not necessarily indicate insulin sensitivity in another tissue type (Faerch et al., *J Physiol.*, 2010, 588:759-764). A decrease in peripheral insulin sensitivity may be affecting glucose control in patients with moderate diabetes more than hepatic insulin sensitivity. A decrease in hepatic insulin sensitivity may be affecting glucose control in patients with severe diabetes more than peripheral insulin sensitivity. Accordingly, a drug that more specifically affects a type of insulin sensitivity may be useful for treating moderate versus severe diabetes. For example, a drug that increases peripheral insulin sensitivity may be more useful in improving moderate diabetes in a patient, while a drug that increases hepatic insulin sensitivity may be more useful in improving severe diabetes in a patient because the liver plays a bigger role in causing fasting hyperglycemia in severely diabetic patients compared to those with mild to moderate diabetes.

"Internucleoside linkage" refers to the chemical bond between nucleosides.

"Intravenous administration" means administration into a vein.

"Linked nucleosides" means adjacent nucleosides which are bonded together.

"Lipid-lowering" means a reduction in one or more lipids in a subject. "Lipid-raising" means an increase in a lipid (e.g., HDL) in a subject. Lipid-lowering or lipid-raising can occur with one or more doses over time.

"Lipid-lowering therapy" or "lipid lowering agent" means a therapeutic regimen provided to a subject to reduce one or more lipids in a subject. In certain embodiments, a lipid-lowering therapy is provided to reduce one or more of CETP, ApoB, total cholesterol, LDL-C, VLDL-C, IDL-C, non-HDL-C, triglycerides, small dense LDL particles, and Lp(a) in a subject. Examples of lipid-lowering therapy include statins, fibrates, MTP inhibitors.

"Lipid profile" means means a summary of the lipid state of a subject as measured by a panel of physiological markers. Physiological markers that can be assessed as part of a lipid profile include, but are not limited to, TG, non-HDL-C, VLDL-C, ApoCIII containing VLDL, ApoB, LDL-C and HDL-C. An "improved lipid profile" can include one or more of: decreased TG, non-HDL-C, VLDL-C, ApoCIII containing VLDL, ApoB and LDL-C; and increased HDL.

"Lipoprotein", such as VLDL, LDL and HDL, refers to a group of proteins found in the serum, plasma and lymph and are important for lipid transport. The chemical composition of each lipoprotein differs in that the HDL has a higher proportion of protein versus lipid, whereas the VLDL has a lower proportion of protein versus lipid.

"Lipoprotein Lipase" or "LPL" refers to an enzyme that hydrolyzes TGs found in lipoproteins, such as CM or VLDL, into free fatty acids and monoacylglycerols. LPL requires apo C-II as a cofactor to function in hydrolyzing TGs. LPL is mainly produced in skeletal muscle, fat tissue, and heart muscle. Hydrolysis and removal of TG from CM and VLDL normally protects against excessive postprandial rise in CM mass and TG.

"Low density lipoprotein-cholesterol (LDL-C)" means cholesterol carried in low density lipoprotein particles. Concentration of LDL-C in serum (or plasma) is typically quantified in mg/dL or nmol/L. "Serum LDL-C" and "plasma LDL-C" mean LDL-C in the serum and plasma, respectively.

"Major risk factors" refers to factors that contribute to a high risk for a particular disease or condition. For example, major risk factors for coronary heart disease include, without limitation, cigarette smoking, hypertension, low HDL-C, family history of coronary heart disease, age, and other factors disclosed herein.

"Metabolic disorder" or "metabolic disease" refers to a condition characterized by an alteration or disturbance in metabolic function. "Metabolic" and "metabolism" are terms well known in the art and generally include the whole range of biochemical processes that occur within a living organism. Metabolic disorders or diseases include, but are not limited to, hyperglycemia, prediabetes, diabetes (type 1 and type 2), obesity, insulin resistance, metabolic syndrome and dyslipidemia due to type 2 diabetes.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Mismatch" or "non-complementary nucleobase" refers to the case when a nucleobase of a first nucleic acid is not capable of pairing with the corresponding nucleobase of a second or target nucleic acid.

"Mixed dyslipidemia" means a condition characterized by elevated cholesterol and elevated triglycerides.

"Modified internucleoside linkage" refers to a substitution or any change from a naturally occurring internucleoside bond. For example, a phosphorothioate linkage is a modified internucleoside linkage.

"Modified nucleobase" refers to any nucleobase other than adenine, cytosine, guanine, thymidine, or uracil. For example, 5-methylcytosine is a modified nucleobase. An "unmodified nucleobase" means the purine bases adenine (A) and guanine (G), and the pyrimidine bases thymine (T), cytosine (C), and uracil (U).

"Modified nucleoside" means a nucleoside having at least one modified sugar moiety, and/or modified nucleobase.

"Modified nucleotide" means a nucleotide having at least one modified sugar moiety, modified internucleoside linkage and/or modified nucleobase.

"Modified oligonucleotide" means an oligonucleotide comprising at least one modified nucleotide.

"Modified sugar" refers to a substitution or change from a natural sugar. For example, a 2'-O-methoxyethyl modified sugar is a modified sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids (ssDNA), double-stranded nucleic acids (dsDNA), small interfering ribonucleic acids (siRNA), and microRNAs (miRNA). A nucleic acid may also comprise a combination of these elements in a single molecule.

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the oligonucleotide and the target nucleic acid are considered to be complementary at that nucleobase pair.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base, and not necessarily the linkage at one or more positions of an oligomeric compound; for example nucleoside mimetics having morpholino, cyclohexenyl, cyclohexyl, tetrahydropyranyl, bicyclo or tricyclo sugar mimetics such as non-furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

"Oligomeric compound" or "oligomer" means a polymer of linked monomeric subunits which is capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleotide" means a polymer of linked nucleosides each of which can be modified or unmodified, independent from one another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, chronic, short or intermittent.

"Peptide" means a molecule formed by linking at least two amino acids by amide bonds. Peptide refers to polypeptides and proteins.

"Pharmaceutical agent" means a substance that provides a therapeutic benefit when administered to an individual. For example, in certain embodiments, an antisense oligonucleotide targeted to ApoCIII is pharmaceutical agent.

"Pharmaceutical composition" or "composition" means a mixture of substances suitable for administering to an individual. For example, a pharmaceutical composition may comprise one or more active agents and a pharmaceutical carrier, such as a sterile aqueous solution.

"Pharmaceutically acceptable carrier" means a medium or diluent that does not interfere with the structure of the compound. Certain of such carriers enable pharmaceutical compositions to be formulated as, for example, tablets, pills, dragees, capsules, liquids, gels, syrups, slurries, suspension and lozenges for the oral ingestion by a subject. Certain of such carriers enable pharmaceutical compositions to be formulated for injection, infusion or topical administration. For example, a pharmaceutically acceptable carrier can be a sterile aqueous solution.

"Pharmaceutically acceptable derivative" or "salts" encompasses derivatives of the compounds described herein such as solvates, hydrates, esters, prodrugs, polymorphs, isomers, isotopically labelled variants, pharmaceutically acceptable salts and other derivatives known in the art.

"Pharmaceutically acceptable salts" means physiologically and pharmaceutically acceptable salts of antisense compounds, i.e., salts that retain the desired biological activity of the parent compound and do not impart undesired toxicological effects thereto. The term "pharmaceutically acceptable salt" or "salt" includes a salt prepared from pharmaceutically acceptable non-toxic acids or bases, including inorganic or organic acids and bases. Pharmaceutically acceptable salts of the compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the compounds described herein are in the form of a sodium salt.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form (i.e., a drug) within the body or cells thereof by the action of endogenous enzymes or other chemicals or conditions.

"Raise" means to increase in amount. For example, to raise plasma HDL levels means to increase the amount of HDL in the plasma.

"Ratio of TG to HDL" means the TG levels relative to HDL levels. The occurrence of high TG and/or low HDL has been linked to cardiovascular disease incidence, outcomes and mortality. "Improving the ratio of TG to HDL" means to decrease TG and/or raise HDL levels.

"Reduce" means to bring down to a smaller extent, size, amount, or number. For example, to reduce plasma triglyceride levels means to bring down the amount of triglyceride in the plasma.

"Region" or "target region" is defined as a portion of the target nucleic acid having at least one identifiable structure, function, or characteristic. For example, a target region may encompass a 3' UTR, a 5' UTR, an exon, an intron, an exon/intron junction, a coding region, a translation initiation region, translation termination region, or other defined nucleic acid region. The structurally defined regions for ApoCIII can be obtained by accession number from sequence databases such as NCBI and such information is incorporated herein by reference. In certain embodiments, a target region may encompass the sequence from a 5' target site of one target segment within the target region to a 3' target site of another target segment within the target region.

"Ribonucleotide" means a nucleotide having a hydroxy at the 2' position of the sugar portion of the nucleotide. Ribonucleotides can be modified with any of a variety of substituents.

"Second agent" or "second therapeutic agent" means an agent that can be used in combination with a "first agent". A second therapeutic agent can include, but is not limited to, an siRNA or antisense oligonucleotide including antisense oligonucleotides targeting ApoCIII. A second agent can also include anti-ApoCIII antibodies, ApoCIII peptide inhibitors, DGAT1 inhibitors, cholesterol lowering agents, lipid lowering agents, glucose lowering agents and anti-inflammatory agents.

"Segments" are defined as smaller, sub-portions of regions within a nucleic acid. For example, a "target segment" means the sequence of nucleotides of a target nucleic acid to which one or more antisense compounds is targeted. "5' target site" refers to the 5'-most nucleotide of a target segment. "3' target site" refers to the 3'-most nucleotide of a target segment.

"Shortened" or "truncated" versions of antisense oligonucleotides or target nucleic acids taught herein have one, two or more nucleosides deleted.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity to a target nucleic acid to induce a desired effect, while exhibiting minimal or no effects on non-target nucleic acids under conditions in which specific binding is desired, i.e. under physiological conditions in the case of in vivo assays and therapeutic treatments.

"Subcutaneous administration" means administration just below the skin.

"Subject" means a human or non-human animal selected for treatment or therapy.

"Symptom of cardiovascular disease or disorder" means a phenomenon that arises from and accompanies the cardiovascular disease or disorder and serves as an indication of it. For example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever are symptoms of cardiovascular disease or disorder.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Therapeutic lifestyle change" means dietary and lifestyle changes intended to lower fat/adipose tissue mass and/or cholesterol. Such change can reduce the risk of developing cardiovascular and/or metabolic diseases, and includes recommendations for dietary intake of total daily calories, total fat, saturated fat, polyunsaturated fat, monounsaturated fat, carbohydrate, protein, cholesterol, insoluble fiber, as well as recommendations for physical activity.

"Treat" refers to administering a compound of the invention to effect an alteration or improvement of a disease, disorder, or condition.

"Triglyceride" or "TG" means a lipid or neutral fat consisting of glycerol combined with three fatty acid molecules.

"Type 2 diabetes," (also known as "type 2 diabetes mellitus", "diabetes mellitus, type 2", "non-insulin-dependent diabetes (NIDDM)", "obesity related diabetes", or "adult-onset diabetes") is a metabolic disorder that is primarily characterized by insulin resistance, relative insulin deficiency, and hyperglycemia.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means one or a plurality of nucleosides modified to impart to an oligonucleotide properties such as enhanced inhibitory activity, increased binding affinity for a target nucleic acid, or resistance to degradation by in vivo nucleases.

Certain Embodiments

Certain embodiments provide an ApoCIII specific inhibitor. In certain embodiments, the ApoCIII specific inhibitor is a nucleic acid capable of inhibiting the expression of ApoCIII. In certain embodiments, the nucleic acid is an antisense compound targeting ApoCIII. In certain embodiments, the antisense compound is an antisense oligonucleotide. In certain embodiments, the antisense oligonucleotide is a modified oligonucleotide. In certain embodiments, the antisense compound has a sequence complementary to any of the sequences set forth in GENBANK Accession No. NM_000040.1 (incorporated herein as SEQ ID NO: 1), GENBANK Accession No. NT_033899.8 truncated from nucleotides 20262640 to 20266603 (incorporated herein as SEQ ID NO: 2), and GenBank Accession No. NT_035088.1 truncated from nucleotides 6238608 to U.S. Pat. No. 6,242,565 (incorporated herein as SEQ ID NO: 3). In certain embodiments, the antisense compound is at least 70%, at least 75%, at least 80%, at least 85%, at least 90%, at least 95%, at least 98% or at least 100% complementary to SEQ ID NO: 1, SEQ ID NO: 2 or SEQ ID NO: 3. In certain embodiments, the ApoCIII specific inhibitors are for use in a subject to treat, prevent, delay and/or ameliorate diabetes. In certain embodiments, the subject is prediabetic. In certain embodiments, the subject has type II diabetes. In certain embodiments, the subject has moderately controlled type II diabetes. In certain embodiments, the ApoCIII specific inhibitors are for use in a subject to improve peripheral insulin sensitivity, lower free fatty acids, reduce intramyocellular triglyceride deposition, improve a lipid profile, and/or improve a diabetic profile.

In certain embodiments, the antisense compound comprises at least 8 nucleobases of the sequence of SEQ ID NO: 4. In certain embodiments, the antisense compound comprises the sequence of SEQ ID NO: 4. In certain embodiments, the antisense compound consists of the sequence of SEQ ID NO: 4. In certain embodiments, the antisense compound is for use in a subject to treat, prevent, delay and/or ameliorate diabetes. In certain embodiments, the subject is prediabetic. In certain embodiments, the subject has type II diabetes. In certain embodiments, the subject has moderately controlled type II diabetes. In certain embodiments, the antisense compound is for use in a subject to improve peripheral insulin sensitivity, lower free fatty acids, reduce intramyocellular triglyceride deposition, improve a lipid profile, and/or improve a diabetic profile.

In certain embodiments, the antisense compound has a nucleobase sequence comprising at least 8 contiguous nucleobases of a sequence selected from any sequence disclosed in U.S. Pat. No. 7,598,227, U.S. Pat. No. 7,750,141, PCT Publication WO 2004/093783 or PCT Publication WO 2012/149495, all incorporated-by-reference herein. In certain embodiments, the antisense compound has a sequence selected from any sequence disclosed in U.S. Pat. No. 7,598,227, U.S. Pat. No. 7,750,141, PCT Publication WO 2004/093783 or PCT Publication WO 2012/149495, all incorporated-by-reference herein. In certain embodiments, the antisense compound is for use in a subject to treat, prevent, delay and/or ameliorate diabetes. In certain embodiments, the subject is prediabetic. In certain embodiments, the subject has type II diabetes. In certain embodiments, the subject has moderately controlled type II diabetes. In certain embodiments, the antisense compound is for use in a subject to improve peripheral insulin sensitivity, lower free fatty acids, reduce intramyocellular triglyceride deposition, improve a lipid profile, and/or improve a diabetic profile.

In certain embodiments, the antisense compound is single-stranded modified oligonucleotide. In certain embodiments, the antisense compound is for use in a subject to treat, prevent, delay and/or ameliorate diabetes. In certain embodiments, the subject is prediabetic. In certain embodiments, the subject has type II diabetes. In certain embodiments, the subject has moderately controlled type II diabetes. In certain embodiments, the antisense compound is for use in a subject to improve peripheral insulin sensitivity, lower free fatty acids, reduce intramyocellular triglyceride deposition, improve a lipid profile, and/or improve a diabetic profile.

In certain embodiments, the antisense compound consists of 12-30 linked nucleosides. In certain embodiments, the antisense compound consists of 20 linked nucleosides. In certain embodiments, the antisense compound consists of 20 linked nucleosides with the nucleobase sequence of SEQ ID NO: 4. In certain embodiments, the antisense compound is for use in a subject to treat, prevent, delay and/or ameliorate diabetes. In certain embodiments, the subject is prediabetic. In certain embodiments, the subject has type II diabetes. In certain embodiments, the subject has moderately controlled type II diabetes. In certain embodiments, the antisense compound is for use in a subject to improve peripheral insulin sensitivity, lower free fatty acids, reduce intramyocellular triglyceride deposition, improve a lipid profile, and/or improve a diabetic profile.

In certain embodiments, the antisense compound comprises at least one modified internucleoside linkage. In certain embodiments, the modified internucleoside linkage is a phosphorothioate (PS) internucleoside linkage. In certain embodiments, each internucleoside linkage is a phosphorothioate internucleoside linkage. In certain embodiments, the antisense compound is for use in a subject to treat, prevent, delay and/or ameliorate diabetes. In certain embodiments, the subject is prediabetic. In certain embodiments, the subject has type II diabetes. In certain embodiments, the subject has moderately controlled type II diabetes. In certain embodiments, the antisense compound is for use in a subject to improve peripheral insulin sensitivity, lower free fatty acids, reduce intramyocellular triglyceride deposition, improve a lipid profile, and/or improve a diabetic profile.

In certain embodiments, the antisense compound comprises at least one nucleoside comprising a modified sugar. In certain embodiments, the at least one modified sugar is a bicyclic sugar. In certain embodiments, the at least one modified sugar comprises a 2'-O-methoxyethyl. In certain embodiments, the at least one modified sugar comprises a cEt. In certain embodiments, the antisense compound is for use in a subject to treat, prevent, delay and/or ameliorate diabetes. In certain embodiments, the subject is prediabetic. In certain embodiments, the subject has type II diabetes. In certain embodiments, the subject has moderately controlled type II diabetes. In certain embodiments, the antisense compound is for use in a subject to improve peripheral insulin sensitivity, lower free fatty acids, reduce intramyocellular triglyceride deposition, improve a lipid profile, and/or improve a diabetic profile.

In certain embodiments, the antisense compound comprises at least one nucleoside comprising a modified nucleobase. In certain embodiments, the modified nucleobase is a 5-methylcytosine. In certain embodiments, the antisense compound is for use in a subject to treat, prevent, delay and/or ameliorate diabetes. In certain embodiments, the subject is prediabetic. In certain embodiments, the subject has type II diabetes. In certain embodiments, the subject has moderately controlled type II diabetes. In certain embodiments, the antisense compound is for use in a subject to improve peripheral insulin sensitivity, lower free fatty acids, reduce intramyocellular triglyceride deposition, improve a lipid profile, and/or improve a diabetic profile.

In certain embodiments, the antisense compound comprises an antisense oligonucleotide comprising: (i) a gap segment consisting of linked deoxynucleosides; (ii) a 5' wing segment consisting of linked nucleosides; and (iii) a 3' wing segment consisting of linked nucleosides; wherein the gap segment is positioned immediately adjacent to and between the 5' wing segment and the 3' wing segment and wherein each nucleoside of each wing segment comprises a modified sugar. In certain embodiments, the antisense compound is for use in a subject to treat, prevent, delay and/or ameliorate diabetes. In certain embodiments, the subject is prediabetic. In certain embodiments, the subject has type II diabetes. In certain embodiments, the subject has moderately controlled type II diabetes. In certain embodiments, the antisense compound is for use in a subject to improve peripheral insulin sensitivity, lower free fatty acids, reduce intramyocellular triglyceride deposition, improve a lipid profile, and/or improve a diabetic profile.

In certain embodiments, the compound comprises an antisense oligonucleotide comprising: (i) a gap segment consisting of 8-12 linked deoxynucleosides; (ii) a 5' wing segment consisting of 1-6 linked nucleosides; and (iii) a 3' wing segment consisting of 1-6 linked nucleosides; wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, and wherein each internucleoside linkage is a phosphorothioate linkage. In certain embodiments, the antisense oligonucleotide is for use in a subject to treat, prevent, delay and/or ameliorate diabetes. In certain embodiments, the subject is prediabetic. In certain embodiments, the subject has type II diabetes. In certain embodiments, the subject has moderately controlled type II diabetes. In certain embodiments, the antisense oligonucleotide is for use in a subject to improve peripheral insulin sensitivity, lower free fatty acids, reduce intramyocellular triglyceride deposition, improve a lipid profile, and/or improve a diabetic profile.

Certain embodiments provide a method of improving insulin sensitivity comprising, selecting a pre-diabetic subject and administering a compound comprising an antisense oligonucleotide 12-30 nucleobases in length targeting ApoCIII thereby improving insulin sensitivity. In certain embodiments, the insulin sensitivity is peripheral insulin sensitivity. In certain embodiments, the subject has high TG levels.

Certain embodiments provide a method of improving insulin sensitivity comprising, selecting a subject with diabetes and administering a compound comprising an antisense oligonucleotide 12-30 nucleobases in length targeting ApoCIII thereby improving insulin sensitivity. In certain embodiments, the insulin sensitivity is peripheral insulin sensitivity. In certain embodiments, the subject has type II diabetes. In certain embodiments, the subject has moderately controlled type II diabetes. In certain embodiments, the subject has high TG levels.

Certain embodiments provide method of improving insulin sensitivity in a subject comprising, selecting a pre-diabetic subject and administering to the subject a therapeutically effective amount of a compound comprising an antisense oligonucleotide having the sequence of SEQ ID NO: 4 wherein the antisense oligonucleotide comprises:
  (a) a gap segment consisting of 10 linked deoxynucleosides;
  (b) a 5' wing segment consisting of 5 linked nucleosides;
  (c) a 3' wing segment consisting 5 linked nucleosides;
wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, wherein each internucleoside linkage is a phosphorothioate linkage, and wherein the insulin sensitivity is improved in the subject. In certain embodiments, the insulin sensitivity is peripheral insulin sensitivity. In certain embodiments, the subject has high TG levels.

Certain embodiments provide method of improving insulin sensitivity in a subject comprising, selecting a subject with diabetes and administering to the subject a therapeutically effective amount of a compound comprising an antisense oligonucleotide having the sequence of SEQ ID NO: 4 wherein the antisense oligonucleotide comprises:
  (a) a gap segment consisting of 10 linked deoxynucleosides;
  (b) a 5' wing segment consisting of 5 linked nucleosides;
  (c) a 3' wing segment consisting 5 linked nucleosides;
wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, wherein each internucleoside linkage is a phosphorothioate linkage, and wherein the insulin sensitivity is improved in the subject. In certain embodiments, the insulin sensitivity is peripheral insulin sensitivity. In certain embodiments, the subject has type II diabetes. In certain embodiments, the subject has moderately controlled type II diabetes. In certain embodiments, the subject has high TG levels.

Certain embodiments provide a method of lowering free fatty acids comprising, selecting a pre-diabetic subject and administering a compound comprising an antisense oligonucleotide 12-30 nucleobases in length targeting ApoCIII, thereby lowering free fatty acids. In certain embodiments, the subject has high TG levels.

Certain embodiments provide a method of lowering free fatty acids comprising, selecting a subject with diabetes and administering a compound comprising an antisense oligonucleotide 12-30 nucleobases in length targeting ApoCIII, thereby lowering free fatty acids. In certain embodiments, the subject has type II diabetes. In certain embodiments, the subject has moderately controlled type II diabetes. In certain embodiments, the subject has high TG levels.

Certain embodiments provide method of lowering free fatty acids in a subject comprising, selecting a pre-diabetic subject and administering to the subject a therapeutically effective amount of a compound comprising an antisense oligonucleotide having the sequence of SEQ ID NO: 4 wherein the antisense oligonucleotide comprises:
  (a) a gap segment consisting of 10 linked deoxynucleosides;

(b) a 5' wing segment consisting of 5 linked nucleosides;
(c) a 3' wing segment consisting 5 linked nucleosides;

wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, wherein each internucleoside linkage is a phosphorothioate linkage, and wherein the free fatty acids are lowered in the subject. In certain embodiments, the subject has high TG levels.

Certain embodiments provide method of lowering free fatty acids in a subject comprising, selecting a subject with diabetes and administering to the subject a therapeutically effective amount of a compound comprising an antisense oligonucleotide having the sequence of SEQ ID NO: 4 wherein the antisense oligonucleotide comprises:

(a) a gap segment consisting of 10 linked deoxynucleosides;
(b) a 5' wing segment consisting of 5 linked nucleosides;
(c) a 3' wing segment consisting 5 linked nucleosides;

wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, wherein each internucleoside linkage is a phosphorothioate linkage, and wherein the free fatty acids are lowered in the subject. In certain embodiments, the subject has type II diabetes. In certain embodiments, the subject has moderately controlled type II diabetes. In certain embodiments, the subject has high TG levels.

Certain embodiments provide method of reducing intramyocellular triglyceride deposition in a subject comprising, selecting a pre-diabetic subject and administering to the subject a therapeutically effective amount of a compound comprising an antisense oligonucleotide having the sequence of SEQ ID NO: 4 wherein the antisense oligonucleotide comprises:

(a) a gap segment consisting of 10 linked deoxynucleosides;
(b) a 5' wing segment consisting of 5 linked nucleosides;
(c) a 3' wing segment consisting 5 linked nucleosides;

wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, wherein each internucleoside linkage is a phosphorothioate linkage, and wherein the intramyocellular triglyceride deposition are reduced in the subject. In certain embodiments, the subject has high TG levels.

Certain embodiments provide a method of reducing intramyocellular triglyceride deposition comprising, selecting a pre-diabetic subject and administering a compound comprising an antisense oligonucleotide 12-30 nucleobases in length targeting ApoCIII, thereby reducing intramyocellular triglyceride deposition. In certain embodiments, the subject has high TG levels.

Certain embodiments provide a method of reducing intramyocellular triglyceride deposition comprising, selecting a subject with diabetes and administering a compound comprising an antisense oligonucleotide 12-30 nucleobases in length targeting ApoCIII, thereby reducing intramyocellular triglyceride deposition. In certain embodiments, the subject has type II diabetes. In certain embodiments, the subject has moderately controlled type II diabetes. In certain embodiments, the subject has high TG levels.

Certain embodiments provide method of reducing intramyocellular triglyceride deposition in a subject comprising, selecting a pre-diabetic subject and administering to the subject a therapeutically effective amount of a compound comprising an antisense oligonucleotide having the sequence of SEQ ID NO: 4 wherein the antisense oligonucleotide comprises:

(a) a gap segment consisting of 10 linked deoxynucleosides;
(b) a 5' wing segment consisting of 5 linked nucleosides;
(c) a 3' wing segment consisting 5 linked nucleosides;

wherein the gap segment is positioned immediately adjacent to and between the 5' wing segment and the 3' wing segment, wherein each nucleoside of each wing segment comprises a 2'-O-methyoxyethyl sugar, wherein each cytosine is a 5'-methylcytosine, wherein each internucleoside linkage is a phosphorothioate linkage, and wherein the intramyocellular triglyceride deposition are reduced in the subject. In certain embodiments, the subject has high TG levels.

Certain embodiments provide method of reducing intramyocellular triglyceride deposition in a subject comprising, selecting a subject with diabetes and administering to the subject a therapeutically effective amount of a compound comprising an antisense oligonucleotide having the sequence of SEQ ID NO: 4 wherein the antisense oligonucleotide comprises:

(a) a gap segment consisting of 10 linked deoxynucleosides;
(b) a 5' wing segment consisting of 5 linked nucleosides;
(c) a 3' wing segment consisting 5 linked nucleosides;

wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, wherein each internucleoside linkage is a phosphorothioate linkage, and wherein the intramyocellular triglyceride deposition are reduced in the subject. In certain embodiments, the subject has type II diabetes. In certain embodiments, the subject has moderately controlled type II diabetes. In certain embodiments, the subject has high TG levels.

Certain embodiments provide a method of improving a lipid profile of a subject comprising, administering a compound comprising an antisense oligonucleotide 12-30 nucleobases in length targeting ApoCIII, wherein free fatty acids, triglycerides, non-HDL-C, VLDL-C, ApoCIII containing VLDL, ApoB and LDL-C are reduced and HDL-C is increased, thereby improving the lipid profile of the subject. In certain embodiments, the subject has high TG levels. In certain embodiments, the subject has low HDL levels. In certain embodiments, the subject is pre-diabetic. In certain embodiments, the subject has type II diabetes. In certain embodiments, the subject has moderately controlled type II diabetes.

Certain embodiments provide a method of improving a lipid profile of a subject comprising, administering a compound comprising an antisense oligonucleotide having the sequence of SEQ ID NO: 4, wherein free fatty acids, triglycerides, non-HDL-C, VLDL-C, ApoCIII containing VLDL, ApoB and LDL-C are reduced and HDL-C is increased and wherein the antisense oligonucleotide comprises:

(a) a gap segment consisting of 10 linked deoxynucleosides;
(b) a 5' wing segment consisting of 5 linked nucleosides;
(c) a 3' wing segment consisting 5 linked nucleosides;

wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, wherein each internucleoside linkage is a phosphorothioate linkage, and wherein the lipid profile is improved in the subject. In certain embodiments, the subject has high TG levels. In certain embodiments, the subject has low HDL levels. In certain embodiments, the subject is pre-diabetic. In certain embodiments, the subject has type II diabetes. In certain embodiments, the subject has moderately controlled type II diabetes.

In certain embodiments, physiological markers that can be assessed as part of a lipid profile include, but are not limited to, TG, non-HDL-C, VLDL-C, ApoCIII containing VLDL, ApoB, LDL-C and HDL-C. In certain embodiments, an improved lipid profile can include one or more of: decreased TG, non-HDL-C, VLDL-C, ApoCIII containing VLDL, ApoB and LDL-C; and increased HDL.

Certain embodiments provide a method of improving a diabetes profile of a subject comprising administering a compound comprising an antisense oligonucleotide 12-30 nucleobases in length targeting ApoCIII, wherein insulin sensitivity index, glucose disposal rate, glucose MCR, glucose metabolism:insulin ration is improved; wherein free fatty acids, triglycerides, non-HDL-C, VLDL-C, ApoCIII containing VLDL, ApoB and LDL-C are reduced and HDL-C is increased, thereby improving the diabetes profile of the subject. In certain embodiments, the subject is pre-diabetic. In certain embodiments, the subject has type II diabetes. In certain embodiments, the subject has moderately controlled type II diabetes. In certain embodiments, the subject has high TG levels.

Certain embodiments provide a method of improving a diabetes profile of a subject comprising administering a compound comprising an antisense oligonucleotide having the sequence of SEQ ID NO: 4, wherein insulin sensitivity index, glucose disposal rate, glucose MCR, glucose metabolism:insulin ration is improved; wherein free fatty acids, triglycerides, non-HDL-C, VLDL-C, ApoCIII containing VLDL, ApoB and LDL-C are reduced and HDL-C is increased and wherein the antisense oligonucleotide comprises:

(a) a gap segment consisting of 10 linked deoxynucleosides;
(b) a 5' wing segment consisting of 5 linked nucleosides;
(c) a 3' wing segment consisting 5 linked nucleosides;

wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, wherein each internucleoside linkage is a phosphorothioate linkage, and wherein the diabetes profile is improved in the subject. In certain embodiments, the subject is pre-diabetic. In certain embodiments, the subject has type II diabetes. In certain embodiments, the subject has moderately controlled type II diabetes. In certain embodiments, the subject has high TG levels.

In certain embodiments, physiological markers that can be assessed as part of a diabetic profile include, but are not limited to, percent glycated albumin, fructosamine levels, percent glycosylated hemoglobin (HbA1c), insulin sensitivity index, peripheral insulin sensitivity, hepatic insulin sensitivity, pancreatic insulin sensitivity, glucose disposal rate, glucose MCR, glucose metabolism:insulin ration, free fatty acids, triglycerides, non-HDL-C, VLDL-C, apoCIII containing VLDL, apoB and LDL-C; and HDL-C. In certain embodiments, an improved diabetic profile can include one or more of: improved insulin sensitivity index, peripheral insulin sensitivity, hepatic insulin sensitivity, pancreatic insulin sensitivity, glucose disposal rate, glucose MCR, glucose metabolism:insulin ration; lowered free fatty acids, triglycerides, non-HDL-C, VLDL-C, apoCIII containing VLDL, apoB, LDL-C, percent glycated albumin, fructosamine levels, percent glycosylated hemoglobin (HbA1c); and increased HDL.

In certain embodiments, the subject is on a stable dose of metformin.

In certain embodiments the subject has fasting triglyceride levels≥200 and ≤500 mg/dl.

In certain embodiments, the subject or animal is human.

In certain embodiments, the antisense compound is parenterally administered. In further embodiments, the parenteral administration is subcutaneous.

In certain embodiments, the antisense compound is co-administered with a second agent or therapy. In certain embodiments, the second agent is an ApoCIII lowering agent, Apo C-II lowering agent, DGAT1 lowering agent, LPL raising agent, cholesterol lowering agent, non-HDL lipid lowering agent, LDL lowering agent, TG lowering agent, HDL raising agent, fish oil, niacin (nicotinic acid), fibrate, statin, DCCR (salt of diazoxide), glucose-lowering agent or anti-diabetic agent. In certain embodiments, the second therapy is dietary fat restriction. In certain embodiments, the second agent is metformin.

In certain embodiments, the antisense compound and the second agent are administered concomitantly or sequentially.

In certain embodiments, the antisense compound is a salt form. In further embodiments, the antisense compound further comprises of a pharmaceutically acceptable carrier or diluent.

Certain embodiments provide an antisense compound comprising an ApoCIII specific antisense oligonucleotide for use in the preparation of a medicament.

Certain embodiments provide a compound comprising an ApoCIII specific antisense oligonucleotide for use in a subject to:

a. improve insulin sensitivity;
b. improve peripheral insulin sensitivity;
c. lower free fatty acids;
d. reduce intramyocellular triglyceride deposition;
e. improve a lipid profile;
f. treat, prevent, delay and/or ameliorate diabetes; and/or
g. improve a diabetic profile.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that it is capable of undergoing hybridization to a target nucleic acid through hydrogen bonding.

Antisense compounds provided herein refer to oligomeric compounds capable of undergoing hybridization to a target nucleic acid through hydrogen bonding. Examples of antisense compounds include single-stranded and double-stranded compounds, such as, antisense oligonucleotides, siRNAs, shRNAs, and miRNAs.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to an ApoCIII nucleic acid is 12 to 30 nucleotides in length. In other words, antisense compounds are from 12 to 30 linked nucleobases. In other embodiments, the antisense compound comprises a modified oligonucleotide consisting of 8 to 80, 10 to 80, 12 to 50, 15 to 30, 18 to 24, 19 to 22, or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values. In some embodiments, the antisense compound is an antisense oligonucleotide.

In certain embodiments, the antisense compound comprises a shortened or truncated modified oligonucleotide. The shortened or truncated modified oligonucleotide can have one or more nucleosides deleted from the 5' end (5' truncation), one or more nucleosides deleted from the 3' end (3' truncation) or one or more nucleosides deleted from the central portion. Alternatively, the deleted nucleosides may be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside may be located at the central portion, 5' or 3' end of the oligonucleotide. When two or more additional nucleosides are present, the added nucleosides may be adjacent to each other, for example, in an oligonucleotide having two nucleosides added to the central portion, to the 5' end (5' addition), or alternatively to the 3' end (3' addition), of the oligonucleotide. Alternatively, the added nucleosides may be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to an ApoCIII nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of a RNA:DNA duplex.

Antisense compounds having a gapmer motif are considered chimeric antisense compounds. In a gapmer an internal region having a plurality of nucleotides that supports RNase H cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH2) n-O-2' bridge, where n=1 or n=2). Preferably, each distinct region comprises uniform sugar moieties. The wing-gap-wing motif is frequently described as "X—Y—Z", where "X" represents the length of the 5' wing region, "Y" represents the length of the gap region, and "Z" represents the length of the 3' wing region. As used herein, a gapmer described as "X—Y—Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same; in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more nucleotides. Thus, gapmers include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 6-8-6, 5-8-5, 1-8-1, 2-6-2, 2-13-2, 1-8-2, 2-8-3, 3-10-2, 1-18-2 or 2-18-2.

In certain embodiments, the antisense compound as a "wingmer" motif, having a wing-gap or gap-wing configuration, i.e. an X—Y or Y—Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13 or 5-13.

In certain embodiments, antisense compounds targeted to an ApoCIII nucleic acid possess a 5-10-5 gapmer motif.

In certain embodiments, an antisense compound targeted to an ApoCIII nucleic acid has a gap-widened motif.

Target Nucleic Acids, Target Regions and Nucleotide Sequences

Nucleotide sequences that encode ApoCIII include, without limitation, the following: GENBANK Accession No. NM_000040.1 (incorporated herein as SEQ ID NO: 1), GENBANK Accession No. NT_033899.8 truncated from nucleotides 20262640 to 20266603 (incorporated herein as SEQ ID NO: 2), and GenBank Accession No. NT_035088.1 truncated from nucleotides 6238608 to U.S. Pat. No. 6,242,565 (incorporated herein as SEQ ID NO: 3)

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for ApoCIII can be obtained by accession number from sequence databases such as NCBI and such information is incorporated herein by reference. In certain embodiments, a target region may encompass the sequence from a 5' target site of one target segment within the target region to a 3' target site of another target segment within the target region.

In certain embodiments, a "target segment" is a smaller, sub-portion of a target region within a nucleic acid. For example, a target segment can be the sequence of nucleotides of a target nucleic acid to which one or more antisense compounds are targeted. "5' target site" refers to the 5'-most nucleotide of a target segment. "3' target site" refers to the 3'-most nucleotide of a target segment.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed, herein.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There can be variation in activity (e.g., as defined by percent reduction of target nucleic acid levels) of the antisense compounds within an active target region. In certain embodiments, reductions in ApoCIII mRNA levels are indicative of inhibition of ApoCIII expression. Reductions in levels of an ApoCIII protein can be indicative of inhibition of target mRNA expression. Further, phenotypic changes can be indicative of inhibition of ApoCIII expression. For example, an increase in HDL level, decrease in LDL level, or decrease in TG level are among phenotypic changes that may be assayed for inhibition of ApoCIII expression. Other phenotypic indications, e.g., symptoms associated with a cardiovascular or metabolic disease, may also be assessed; for example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever.

Hybridization

In some embodiments, hybridization occurs between an antisense compound disclosed herein and an ApoCIII nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art (Sambrook and Russell, Molecular Cloning: A Laboratory Manual, $3^{rd}$ Ed., 2001, CSHL Press). In certain embodiments, the antisense compounds provided herein are specifically hybridizable with an ApoCIII nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an ApoCIII nucleic acid).

An antisense compound may hybridize over one or more segments of an ApoCIII nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 75%, 80%, 85%, 86%, 87%, 88%, 89%, 90%, 91%, 92%, 93%, 94%, 95%, 96%, 97%, 98%, 99%, or 100% complementary to an ApoCIII nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, an antisense compound which is 18 nucleobases in length having 4 (four) non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

In certain embodiments, the antisense compounds provided herein, or specified portions thereof, are fully complementary (i.e. 100% complementary) to a target nucleic acid, or specified portion thereof. For example, an antisense compound may be fully complementary to an ApoCIII nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase(s) can be at the 5' end or 3' end of the antisense compound. Alternatively, the non-complementary nucleobase(s) can be at an internal position of the antisense compound. When two or more non-complementary nucleobases are present, they can be contiguous (i.e. linked) or non-contiguous. In one embodiment, a non-complementary nucleobase is located in the wing segment of a gapmer antisense oligonucleotide.

In certain embodiments, antisense compounds that are, or are up to, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an ApoCIII nucleic acid, or specified portion thereof.

In certain embodiments, antisense compounds that are, or are up to, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an ApoCIII nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds are complementary to at least an 8 nucleobase portion of a target segment. In certain embodiments, the antisense compounds are complementary to at least a 10 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or sequence of a compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides can also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an ApoCIII nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substitutent groups, bridging of non-geminal ring atoms to form bicyclic nucleic acids (BNA), replacement of the ribosyl ring oxygen atom with S, N(R), or C(R$_1$)(R$_2$) (R, R$_1$ and R$_2$ are each independently H, C$_1$-C$_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'-OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—C$_1$-C$_{10}$ alkyl, OCF$_3$, OCH$_2$F, O(CH$_2$)$_2$SCH$_3$, O(CH$_2$)$_2$—O—N(R$_m$)(R$_n$), O—CH$_2$—C(=O)—N(R$_m$)(R$_n$), and O—CH$_2$—C(=O)—N(R$_l$)—(CH$_2$)$_2$—N(R$_m$)(R$_n$), where each R$_l$, R$_m$ and R$_n$ is, independently, H or substituted or unsubstituted C$_1$-C$_{10}$ alkyl.

As used herein, "bicyclic nucleosides" refer to modified nucleosides comprising a bicyclic sugar moiety. Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-(CH$_2$)—O-2' (LNA); 4'-(CH$_2$)—S-2; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see PCT/US2008/068922 published as WO/2009/006478, published Jan. 8, 2009); 4'-CH$_2$—N(OCH$_3$)-2' (and analogs thereof see PCT/US2008/064591 published as WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., *J. Org. Chem.*, 2009, 74, 118-134); and 4'-CH$_2$—C—(=CH$_2$)-2' (and analogs thereof see PCT/US2008/066154 published as WO 2008/154401, published on Dec. 8, 2008).

Further bicyclic nucleosides have been reported in published literature (see for example: Srivastava et al., *J. Am. Chem. Soc.*, 2007, 129(26) 8362-8379; Frieden et al., *Nucleic Acids Research*, 2003, 21, 6365-6372; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wahlestedt et al., *Proc. Natl. Acad. Sci. U.S.A*, 2000, 97, 5633-5638; Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; U.S. Pat. Nos. 7,399,845; 7,053,207; 7,034,133; 6,794,499; 6,770,748; 6,670,461; 6,525,191; 6,268,490; U.S. Patent Publication Nos.: US2008-0039618; US2007-0287831; US2004-0171570; U.S. patent application Ser. Nos. 12/129,154; 61/099,844; 61/097,787; 61/086,231; 61/056,564; 61/026,998; 61/026,995; 60/989,574; International applications WO 2007/134181; WO 2005/021570; WO 2004/106356; WO 94/14226; and PCT International Applications Nos.: PCT/US2008/068922; PCT/US2008/066154; and PCT/US2008/064591). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

In certain embodiments, bicyclic sugar moieties of BNA nucleosides include, but are not limited to, compounds having at least one bridge between the 4' and the 2' carbon atoms of the pentofuranosyl sugar moiety including without limitation, bridges comprising 1 or from 1 to 4 linked groups independently selected from —[C($R_a$)($R_b$)]$_n$—, —C($R_a$)=C($R_b$)—, —C($R_a$)=N—, —C(=N$R_a$)—, —C(=O)—, —C(=S)—, —O—, —Si($R_a$)$_2$—, —S(=O)$_x$—, and —N($R_a$)—; wherein: x is 0, 1, or 2; n is 1, 2, 3, or 4; each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, O$J_1$, N$J_1J_2$, S$J_1$, $N_3$, COO$J_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is, —[C($R_a$)($R_b$)]$_n$—, —[C($R_a$)($R_b$)]$_n$—O—, —C($R_aR_b$)—N(R)—O— or —C($R_aR_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-(CH$_2$)—O-2' bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include those having a 4' to 2' bridge wherein such bridges include without limitation, α-L-4'-(CH$_2$)—O-2', β-D-4'-CH$_2$—O-2', 4'-(CH$_2$)$_2$—O-2', 4'-CH$_2$—O—N(R)-2', 4'-CH$_2$—N(R)—O-2', 4'-CH(CH$_3$)—O-2', 4'-CH$_2$—S-2', 4'-CH$_2$—N(R)-2', 4'-CH$_2$—CH(CH$_3$)-2', and 4'-(CH$_2$)$_3$-2', wherein R is H, a protecting group or $C_1$-$C_{12}$ alkyl.

In certain embodiment, bicyclic nucleosides have the formula:

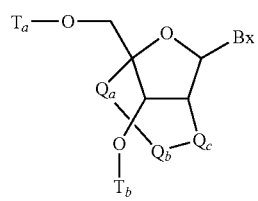

wherein:

Bx is a heterocyclic base moiety;

-$Q_a$-$Q_b$-$Q_c$- is —CH$_2$—N($R_c$)—CH$_2$—, —C(=O)—N($R_c$)—CH$_2$—, —CH$_2$—O—N($R_c$)—, —CH$_2$—N($R_c$)—O— or —N($R_c$)—O—CH$_2$;

$R_c$ is $C_1$-$C_{12}$ alkyl or an amino protecting group; and $T_a$ and $T_b$ are each, independently, H, a hydroxyl protecting group, a conjugate group, a reactive phosphorus group, a phosphorus moiety or a covalent attachment to a support medium.

In certain embodiments, bicyclic nucleosides have the formula:

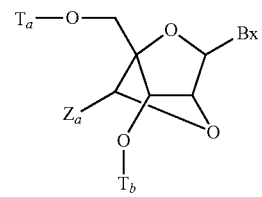

wherein:

Bx is a heterocyclic base moiety;

$T_a$ and $T_b$ are each, independently, H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, O$J_c$, N$J_cJ_d$, S$J_c$, $N_3$, OC(=X)$J_c$, and N$J_c$C(=X)N$J_cJ_d$, wherein each $J_c$, $J_d$ and $J_e$ is, independently, H, $C_1$-$C_6$ alkyl, or substituted $C_1$-$C_6$ alkyl and X is O or N$J_c$.

In certain embodiments, bicyclic nucleosides have the formula:

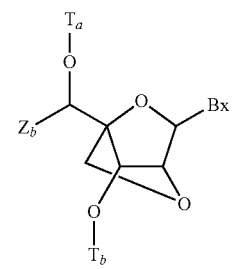

wherein:

Bx is a heterocyclic base moiety;

$T_a$ and $T_b$ are each, independently, H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides have the formula:

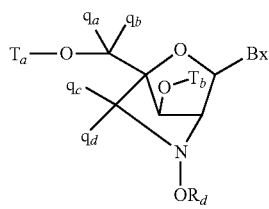

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides have the formula:

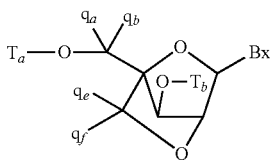

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SOJ_j$, $SO_2J_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'-CH$_2$—O-2' bridge, along with their oligomerization, and nucleic acid recognition properties have been described (Koshkin et al., *Tetrahedron*, 1998, 54, 3607-3630). The synthesis of bicyclic nucleosides has also been described in WO 98/39352 and WO 99/14226.

Analogs of various bicyclic nucleosides that have 4' to 2' bridging groups such as 4'-CH$_2$—O-2' and 4'-CH$_2$—S-2', have also been prepared (Kumar et al., *Bioorg. Med. Chem. Lett.*, 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides have the formula:

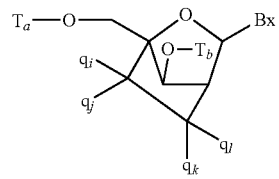

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Frier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.* 2007, 129(26), 8362-8379).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, (F) methyl(methyleneoxy) (4'-CH(CH$_3$)—O-2) BNA (also referred to as constrained ethyl or cEt), (G) methylene-thio (4'-CH$_2$—S-2') BNA, (H) methylene-amino (4'-CH$_2$—N(R)-2) BNA, (I) methyl carbocyclic (4'-CH$_2$—CH(CH$_3$)-2') BNA, (J) propylene carbocyclic (4'-(CH$_2$)$_3$-2') BNA, and (K) vinyl BNA as depicted below.

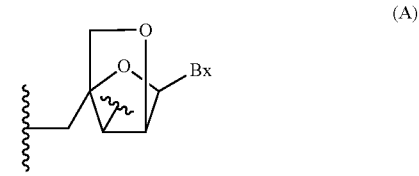

(A)

(B) 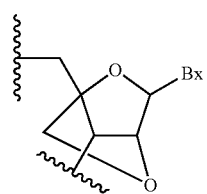

(C) 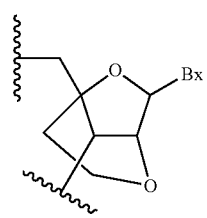

(D) 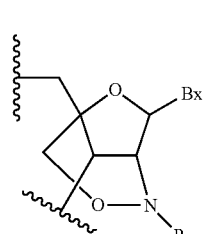

(E) 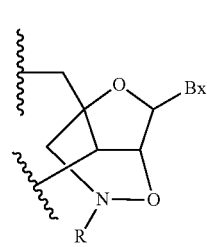

(F) 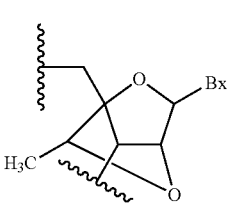

(G) 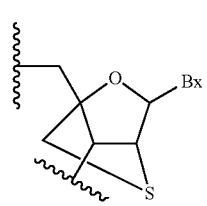

(H) 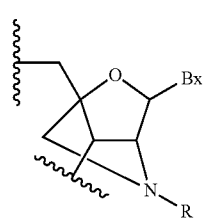

(I) 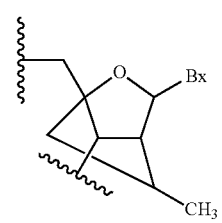

(J) 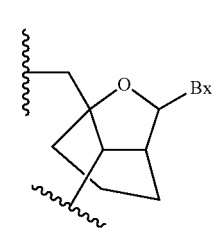

(K) 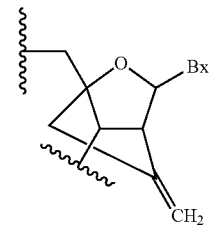

wherein Bx is the base moiety and R is, independently, H, a protecting group, $C_1$-$C_6$ alkyl or $C_1$-$C_6$ alkoxy.

As used herein, the term "modified tetrahydropyran nucleoside" or "modified THP nucleoside" means a nucleoside having a six-membered tetrahydropyran "sugar" substituted for the pentofuranosyl residue in normal nucleosides and can be referred to as a sugar surrogate. Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854) or fluoro HNA (F-HNA) having a tetrahydropyranyl ring system as illustrated below.

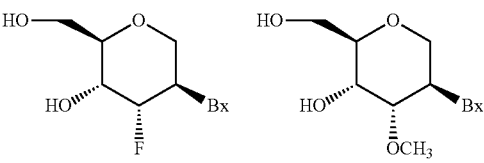

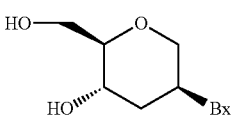

In certain embodiment, sugar surrogates are selected having the formula:

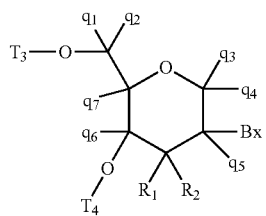

wherein:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to an oligomeric compound or oligonucleotide and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., *Biochemistry*, 2002, 41, 4503-4510; and U.S. Pat. Nos. 5,698,685; 5,166,315; 5,185,444; and 5,034,506). As used here, the term "morpholino" means a sugar surrogate having the following formula:

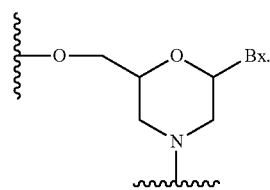

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horvath et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., *Acta Crystallographica, Section F: Structural Biology and Crystallization Communications*, 2005, F61(6), 585-586; Gu et al., *Tetrahedron*, 2004, 60(9), 2111-4123; Gu et al., *Oligonucleotides*, 2003, 13(6), 479-489; Wang et al., *J. Org. Chem.*, 2003, 68, 4499-4505; Verbeure et al., *Nucleic Acids Research*, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

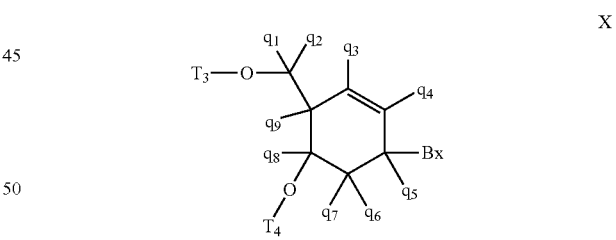

wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J. *Bioorg. & Med. Chem.*, 2002, 10, 841-854). Such ring systems can undergo various additional substitutions to further enhance their activity.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modifed nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—$N(R_m)(R_n)$, or O—$CH_2$—$C(=O)$—$N(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-$OCH_3$", "2'-O-methyl" or "2'-methoxy" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

Methods for the preparations of modified sugars are well known to those skilled in the art. Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-$CH(CH_3)$—O-2') bridging group. In certain embodiments, the (4'-$CH(CH_3)$—O-2') modified nucleosides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine.

Heterocyclic base moieties may include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to an ApoCIII nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense compounds may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compounds targeted to an ApoCIII nucleic acid can be utilized in pharmaceutical compositions by combining the antisense compound with a suitable pharmaceutically acceptable diluent or carrier.

In certain embodiments, the "pharmaceutical carrier" or "excipient" is a pharmaceutically acceptable solvent, suspending agent or any other pharmacologically inert vehicle for delivering one or more nucleic acids to an animal. The excipient can be liquid or solid and can be selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipients, which do not deleteriously react with nucleic acids, suitable for parenteral or non-parenteral administration can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to an ApoCIII nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or an oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of ApoCIII nucleic acids or proteins can be tested in vitro in a variety of cell types. Cell types used for such analyses are available from commercial vendors (e.g. American Type Culture Collection, Manassas, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, Hep3B cells, Huh7 (hepatocellular carcinoma) cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another reagent used to introduce antisense oligonucleotides into cultured cells includes Oligofectamine™ (Invitrogen Life Technologies, Carlsbad, Calif.). Antisense oligonucleotide is mixed with Oligofectamine™ in Opti-MEM™-1 reduced serum medium (Invitrogen Life Technologies, Carlsbad, Calif.) to achieve the desired concentration of oligonucleotide with an Oligofectamine™ to oligonucleotide ratio of approximately 0.2 to 0.8 µL per 100 nM.

Another reagent used to introduce antisense oligonucleotides into cultured cells includes FuGENE 6 (Roche Diagnostics Corp., Indianapolis, Ind.). Antisense oligomeric compound was mixed with FuGENE 6 in 1 mL of serum-free RPMI to achieve the desired concentration of oligonucleotide with a FuGENE 6 to oligomeric compound ratio of 1 to 4 µL of FuGENE 6 per 100 nM.

Another technique used to introduce antisense oligonucleotides into cultured cells includes electroporation (Sambrook and Russell in *Molecular Cloning. A Laboratory Manual*. Third Edition. Cold Spring Harbor Laboratory Press, Cold Spring Harbor, N.Y. 2001).

Cells are treated with antisense oligonucleotides by routine methods. Cells are typically harvested 16-24 hours after antisense oligonucleotide treatment, at which time RNA or protein levels of target nucleic acids are measured by methods known in the art and described herein (Sambrook and Russell in *Molecular Cloning. A Laboratory Manual*. Third Edition. Cold Spring Harbor Laboratory Press, Cold Spring Harbor, N.Y. 2001). In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art (Sambrook and Russell in *Molecular Cloning. A Laboratory Manual*. Third Edition. Cold Spring Harbor Laboratory Press, Cold Spring Harbor, N.Y. 2001). Antisense oligonucleotides are typically used at concentrations ranging from 1 nM to 300 nM when transfected with LIPOFECTAMINE2000® (Invitrogen, Carlsbad, Calif.), Lipofectin® (Invitrogen, Carlsbad, Calif.) or Cytofectin™ (Genlantis, San Diego, Calif.). Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art (Sambrook and Russell in *Molecular Cloning. A Laboratory Manual*. Third Edition. Cold Spring Harbor Laboratory Press, Cold Spring Harbor, N.Y. 2001). RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of an ApoCIII nucleic acid can be assayed in a variety of ways known in the art (Sambrook and Russell in *Molecular Cloning. A Laboratory Manual*. Third Edition. Cold Spring Harbor Laboratory Press, Cold Spring Harbor, N.Y. 2001). For example, target nucleic acid levels can be quantitated by, e.g., Northern blot analysis, competitive polymerase chain reaction (PCR), or quantitative real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT and real-time-PCR reactions are carried out by methods well known to those skilled in the art.

Gene (or RNA) target quantities obtained by real time PCR can be normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Carlsbad, Calif.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems, Foster City, Calif.) is used to measure RIBOGREEN® fluorescence.

Probes and primers are designed to hybridize to an ApoCIII nucleic acid. Methods for designing real-time PCR probes and primers are well known in the art, and may include the use of software such as PRIMER EXPRESS® Software (Applied Biosystems, Foster City, Calif.).

Gene target quantities obtained by RT, real-time PCR can use either the expression level of GAPDH or Cyclophilin A, genes whose expression are constant, or by quantifying total RNA using RiboGreen™ (Molecular Probes, Inc. Eugene, Oreg.). GAPDH or Cyclophilin A expression can be quantified by RT, real-time PCR, by being run simultaneously with the target, multiplexing, or separately. Total RNA was quantified using RiboGreen™ RNA quantification reagent (Molecular Probes, Inc. Eugene, Oreg.).

Analysis of Protein Levels

Antisense inhibition of ApoCIII nucleic acids can be assessed by measuring ApoCIII protein levels. Protein levels of ApoCIII can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS) (Sambrook and Russell in *Molecular Cloning. A Laboratory Manual*. Third Edition. Cold Spring Harbor Laboratory Press, Cold Spring Harbor, N.Y. 2001). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and mouse ApoCIII are commercially available.

In Vivo Testing of Antisense Compounds

Antisense compounds, for example, antisense oligonucleotides, are tested in animals to assess their ability to inhibit expression of ApoCIII and produce phenotypic changes. Testing can be performed in normal animals, or in experimental disease models. For administration to animals, antisense oligonucleotides are formulated in a pharmaceutically acceptable diluent, such as phosphate-buffered saline. Administration includes parenteral routes of administration. Calculation of antisense oligonucleotide dosage and dosing frequency depends upon factors such as route of administration and animal body weight. Following a period of treatment with antisense oligonucleotides, RNA is isolated from tissue and changes in ApoCIII nucleic acid expression are measured. Changes in ApoCIII protein levels are also measured.

Certain Indications

In certain embodiments, provided herein are improved compounds and methods for treating a subject having diabetes, at risk of having diabetes, or a symptom thereof. In certain embodiments, the diabetes, a symptom thereof, is improved. I certain embodiment, the risk of having diabetes is decreased. In certain embodiments, the compound comprises an antisense compound targeted to an ApoCIII.

In certain embodiments, administration of an antisense compound targeted to an ApoCIII nucleic acid to a subject results in reduction of ApoCIII expression by at least about 15, 20, 25, 30, 35, 40, 45, 50, 55, 60, 65, 70, 75, 80, 85, 90, 95 or 99%, or a range defined by any two of these values. In certain embodiments, ApoCIII expression is reduced to ≤50 mg/L, ≤60 mg/L, ≤70 mg/L, ≤80 mg/L, ≤90 mg/L, ≤100 mg/L, ≤110 mg/L, ≤120 mg/L, ≤130 mg/L, ≤140 mg/L, ≤150 mg/L, ≤160 mg/L, ≤170 mg/L, ≤180 mg/L, ≤190 mg/L or ≤200 mg/L.

In certain embodiments, compounds targeted to ApoCIII as described herein improves a diabetic profile and/or a lipid profile by modulating physiological markers or phenotypes in a subject. In certain of the experiments, the compounds can increase or decrease physiological markers or phenotypes compared to untreated subjects. In certain embodiments, the increase or decrease in physiological markers or phenotypes is associated with inhibition of ApoCIII by the compounds described herein.

In certain embodiments, physiological markers or phenotype of a diabetic and/or lipid profile can be quantifiable by standard laboratory tests. In certain embodiments, physiological markers or phenotypes such as HDL can be increased by about 5, 10, 15, 20, 25, 30, 35, 40, 45, 50, 55, 60, 65, 70, 75, 80, 85, 90, 95 or 99%, or a range defined by any two of these values. In certain embodiments, physiological markers or phenotypes such as insulin sensitivity index, glucose level, glucose disposal rate, glucose MCR and/or glucose metabolism:insulin ration are improved by about 5, 10, 15, 20, 25, 30, 35, 40, 45, 50, 55, 60, 65, 70, 75, 80, 85, 90, 95 or 99%, or a range defined by any two of these values. In certain embodiments, physiological markers or phenotypes such as wherein free fatty acids, insulin resistance, TG, non-HDL-C, VLDL-C, ApoCIII containing VLDL, ApoB and/or LDL-C are reduced by about 5, 10, 15, 20, 25, 30, 35, 40, 45, 50, 55, 60, 65, 70, 75, 80, 85, 90, 95 or 99%, or a range defined by any two of these values.

Administration

The compounds or pharmaceutical compositions of the present invention can be administered in a number of ways depending upon whether local or systemic treatment is desired and upon the area to be treated. Administration can be oral or parenteral.

In certain embodiments, the compounds and compositions as described herein are administered parenterally. Parenteral administration includes intravenous, intra-arterial, subcutaneous, intraperitoneal or intramuscular injection or infusion.

In certain embodiments, parenteral administration is by infusion. Infusion can be chronic or continuous or short or intermittent. In certain embodiments, infused pharmaceutical agents are delivered with a pump. In certain embodiments, the infusion is intravenous.

In certain embodiments, parenteral administration is by injection. The injection can be delivered with a syringe or a pump. In certain embodiments, the injection is a bolus injection. In certain embodiments, the injection is administered directly to a tissue or organ. In certain embodiments, parenteral administration is subcutaneous.

In certain embodiments, formulations for parenteral administration can include sterile aqueous solutions which can also contain buffers, diluents and other suitable additives such as, but not limited to, penetration enhancers, carrier compounds and other pharmaceutically acceptable carriers or excipients.

In certain embodiments, formulations for oral administration of the compounds or compositions of the invention can include, but is not limited to, pharmaceutical carriers, excipients, powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In certain embodiments, oral formulations are those in which compounds of the invention are administered in conjunction with one or more penetration enhancers, surfactants and chelators.

Dosing

In certain embodiments, pharmaceutical compositions are administered according to a dosing regimen (e.g., dose, dose frequency, and duration) wherein the dosing regimen can be selected to achieve a desired effect. The desired effect can be, for example, reduction of ApoCIII or the prevention, reduction, amelioration or slowing the progression of a disease or condition associated with a cardiovascular and/or metabolic disease, disorder or condition, or symptom thereof.

In certain embodiments, the variables of the dosing regimen are adjusted to result in a desired concentration of pharmaceutical composition in a subject. "Concentration of pharmaceutical composition" as used with regard to dose regimen can refer to the compound, oligonucleotide, or active ingredient of the pharmaceutical composition. For example, in certain embodiments, dose and dose frequency are adjusted to provide a tissue concentration or plasma concentration of a pharmaceutical composition at an amount sufficient to achieve a desired effect.

Dosing is dependent on severity and responsiveness of the disease state to be treated, with the course of treatment lasting from several days to several months, or until a cure is effected or a diminution of the disease state is achieved. Dosing is also dependent on drug potency and metabolism. In certain embodiments, dosage is from 0.01 µg to 100 mg per kg of body weight, or within a range of 0.001 mg-1000 mg dosing, and may be given once or more daily, weekly, monthly or yearly, or even once every 2 to 20 years. Following successful treatment, it may be desirable to have the subject undergo maintenance therapy to prevent the recurrence of the disease state, wherein the oligonucleotide is administered in maintenance doses, ranging from 0.01 µg to 100 mg per kg of body weight, once or more daily, to once every 20 years or ranging from 0.001 mg to 1000 mg dosing.

Certain Combination Therapies

In certain embodiments, a first agent comprising the compound described herein is co-administered with one or more secondary agents. In certain embodiments, such second agents are designed to treat the same disease, disorder, or condition as the first agent described herein. In certain embodiments, such second agents are designed to treat a different disease, disorder, or condition as the first agent described herein. In certain embodiments, a first agent is designed to treat an undesired side effect of a second agent. In certain embodiments, second agents are co-administered with the first agent to treat an undesired effect of the first agent. In certain embodiments, such second agents are designed to treat an undesired side effect of one or more pharmaceutical compositions as described herein. In certain embodiments, second agents are co-administered with the first agent to produce a combinational effect. In certain embodiments, second agents are co-administered with the first agent to produce a synergistic effect. In certain embodiments, the co-administration of the first and second agents permits use of lower dosages than would be required to achieve a therapeutic or prophylactic effect if the agents were administered as independent therapy.

In certain embodiments, one or more compositions described herein and one or more other pharmaceutical agents are administered at the same time. In certain embodiments, one or more compositions of the invention and one or more other pharmaceutical agents are administered at different times. In certain embodiments, one or more compositions described herein and one or more other pharmaceutical agents are prepared together in a single formulation. In certain embodiments, one or more compositions described herein and one or more other pharmaceutical agents are prepared separately.

In certain embodiments, second agents include, but are not limited to, ApoCIII lowering agent, DGAT1 inhibitor, LPL raising agent, cholesterol lowering agent, non-HDL lipid lowering (e.g., LDL) agent, HDL raising agent, fish oil, niacin (nicotinic acid), fibrate, statin, DCCR (salt of diazoxide), glucose-lowering agent and/or anti-diabetic agents. In certain embodiments, the first agent is administered in combination with the maximally tolerated dose of the second agent. In certain embodiments, the first agent is administered to a subject that fails to respond to a maximally tolerated dose of the second agent.

Examples of ApoCIII lowering agents include an ApoCIII antisense oligonucleotide different from the first agent, a fibrate or an Apo B antisense oligonucleotide.

An example of a DGAT1 inhibitor is LCQ908 (Novartis Pharmaceuticals) currently being tested in a Phase 3 clinical trial for treating Familial Chylomicronemia Syndrome.

LPL raising agents include gene therapy agents that raise the level of LPL. Examples of such agents include copies of normal genes that supplement the lack of the normal gene. For example, Glybera$^R$ raises LPL levels by providing normal copies of the LPL gene to supplement a lack of the normal LPL gene. In other examples, the LPL raising agent includes normal copies of ApoC-II, GPIHBP1, APOA5, LMF1 or other genes that, when mutated, can lead to dysfunctional LPL. In certain embodiments, the combination of the first agent (e.g., ApoCIII ASO) and the second agent (e.g., Glybera) provides an additive or synergistic effect.

Examples of glucose-lowering and/or anti-diabetic agents include, but is not limited to, a therapeutic lifestyle change, PPAR agonist, a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, metformin, sulfonylurea, rosiglitazone, meglitinide, thiazolidinedione, alpha-glucosidase inhibitor and the like. The sulfonylurea can be acetohexamide, chlorpropamide, tolbutamide, tolazamide, glimepiride, a glipizide, a glyburide, or a gliclazide. The meglitinide can be nateglinide or repaglinide. The thiazolidinedione can be pioglitazone or rosiglitazone. The alpha-glucosidase can be acarbose or miglitol.

The cholesterol or lipid lowering therapy can include, but is not limited to, a therapeutic lifestyle change, statins, bile acids sequestrants, nicotinic acid and fibrates. The statins can be atorvastatin, fluvastatin, lovastatin, pravastatin, rosuvastatin and simvastatin and the like. The bile acid sequestrants can be colesevelam, cholestyramine, colestipol and the like. The fibrates can be gemfibrozil, fenofibrate, clofibrate and the like. The therapeutic lifestyle change can be dietary fat restriction. The bile acids sequestrant can be colesevelam, cholestyramine, colestipol or the like.

HDL increasing agents include cholesteryl ester transfer protein (CETP) inhibiting drugs (such as Torcetrapib), peroxisome proliferation activated receptor agonists, Apo-A1, Pioglitazone and the like.

Certain Compounds

We have previously disclosed compositions comprising antisense compounds targeting ApoCIII and methods for inhibiting ApoCIII by the antisense compounds in US 20040208856 (U.S. Pat. No. 7,598,227), US 20060264395 (U.S. Pat. No. 7,750,141), WO 2004/093783 and WO 2012/149495, all incorporated-by-reference herein. In these applications, a series of antisense compounds was designed to target different regions of the human ApoCIII RNA, using published sequences (nucleotides 6238608 to 6242565 of GenBank accession number NT_035088.1, representing a genomic sequence, incorporated herein as SEQ ID NO: 3, and GenBank accession number NM_000040.1, incorporated herein as SEQ ID NO: 1). The compounds were chimeric oligonucleotides ("gapmers") 20 nucleotides in length, composed of a central "gap" region consisting of ten 2'-deoxynucleotides, which was flanked on both sides (5' and 3' directions) by five-nucleotide "wings". The wings were composed of 2'-O-(2-methoxyethyl) nucleotides, also known as (2'-MOE) nucleotides. The internucleoside (backbone) linkages were phosphorothioate (P=S) throughout the oligonucleotide. All cytosine residues were 5-methylcytosines. An exemplary compound described in these applications is ISIS 304801 (AGCTTCTTGTCCAGCTTTAT, (SEQ ID NO: 4)).

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: ISIS 304801 Phase II Clinical Trial

A randomized, double-blind, placebo-controlled study to evaluate the effect of ISIS 304801 vs. placebo on ApoC-III levels, high triglyceride levels and Type 2 diabetes was conducted (http://clinicaltrials.gov/ct2/show/NCT01647308?term=isis&rank=5). The patients were diagnosed with hypertriglyceridemia and Type 2 diabetes for at least 6 months and have been on a stable dose of metformin (≥1 g/day) for at least 4 weeks prior to screening for the study. Their fasting triglyceride levels were between about 200 and 500 mg/dL and HbA1C levels were greater than or equal to 7% and less than 9%. Further baseline characteristics are provided in Table 1 below.

TABLE 1

Baseline characteristics of patients in the Phase 2 study

| | Placebo (n = 4) | 300 mg (n = 7) |
|---|---|---|
| Gender (M:F) | 3:1 | 5:2 |
| Age (yrs) | 53 | 57 |
| BMI (kg/m$^2$) | 34 | 34 |
| Fasting Glucose (mg/dL) | 185 | 168 |
| HbA1c (%) | 7.8 | 7.8 |
| Fasting Lipids & Lipoproteins, mg/dL | | |
| ApoC- III (mg/dL) | 12 | 14 |
| Triglycerides (mg/dL) | 223 | 259 |
| HDL-C (ppt; mg/dL) | 39 | 43 |
| Non-HDL-C (calc; mg/dL) | 188 | 178 |
| Apo B (mg/dL) | 128 | 115 |
| LDL-C (ultacent; mg/dL) | 147 | 126 |
| Total Cholesterol (mg/dL) | 227 | 221 |
| VLDL-ApoC-III (mg/dL) | 6 | 7 |
| VLDL-C (mg/dL) | 42 | 51 |

The patients were randomized 2:1 for treatment with ISIS 304801 or placebo. For each patient, the participation period consists of a ≤4-week screening period, a 2-day study qualification/baseline assessment period, a 13-week treatment period, and a post-treatment evaluation period of 13 weeks. Concomitant medications and adverse events (AEs) will be recorded throughout all periods of the study.

Study Drug and Treatment

A solution of ISIS 304801 (200 mg/mL, 1.0 mL) contained in 2-mL stoppered glass vials was provided. It was designated as the active drug.

The placebo for this study was 0.9% sterile saline. Active drug and placebo are both referred to as Study Drug.

ISIS 304801 solution and placebo were prepared by an unblinded pharmacist (or qualified delegate). Vials were for single-use only. A trained professional, blinded to the identity of the drug, administered the Study Drug. The Study Drug was administered as a SC injection in the abdomen, thigh, or outer area of the upper arm on each dosing day. Each dose of 300 mg was administered as a single 1.5 ml SC injection.

Patients received 15 doses of Study Drug administered by SC injection for 13 weeks (Days 1, 3, 5, 8, 15, 22, 29, 36, 43, 50, 57, 64, 71, 78, and 85).

Patients completed the treatment visits on Day 1±0 days and on Day 3, 5, 8, 15, 22, 29, 36, 43, 50, 57, 64, 71, 78, and 85 within ±1 day. Patients completed the follow-up visits on Days 90-92, Day 99±1 day, Day 127±3 days, and the study terminated with a visit on Day 176 within ±5 days of the scheduled visit date.

Patients fasted overnight and had blood samples collected on Days −2 and −1 and during the treatment visits on Days 1, 3, 5, 8, 15, 29, and 57, and during the follow-up visits on Days 90, 91, 92, 99, 127, and 176. Patients had hyperinsulinemic euglycemic clamp procedures performed on Days 1 and 92.

There were no safety issues with no drug-related significant adverse events and no clinically relevant changes in laboratory assessments for safety parameters. Specifically, there were no clinically relevant liver enzyme elevations. The treatment was tolerable to all patients; there were no discontinuations and a low incidence of injection site reactions, which were primarily mild erythema. There were no-flu-like symptoms after administration of the injections.

Clinical and Laboratory Procedures

Biological Samples

Blood and other tissue samples were collected during patients' visits to the testing center. The samples were measured for various biomarkers by standard laboratory procedures.

Glucose Turnover

Patients received a low primed-continuous infusion of [6,6-2H2] glucose for the measurement of endogenous glucose production. The primed-continuous infusion (5 mg/kg body weight injected over 3 minutes, followed by a constant infusion of 0.05 mg/kg body weight/min) commenced at approximately 1 AM prior to the clamp and was continued during the clamp. After at least a 6-hour equilibration period during which the tracer enrichment has reached steady-state, blood samples were taken at 10-min intervals over a 30-min period (4 samples) for calculation of basal endogenous glucose production. Immediately after collecting the last baseline sample, the rate of the continuous [6,6-2H2] glucose infusion was reduced by 50%, i.e., at the commencement of the first step of the clamp. Blood samples were taken before the start of the isotope infusion and during the [6,6-2H2] glucose infusion to determine plasma glucose enrichments that were used to calculate basal endogenous glucose production. [6,6-2H2] glucose isotope ratios in blood were measured using isotope ratio mass spectrometry. Endogenous glucose production was calculated from the dilution of [6,6-2H2] glucose using the non-steady state method of Steele (Steele, R., *Ann N Y Acad Sci,* 1959, 82:420-430).

Two-Step Hyperinsulinemic-Euglycemic Clamp

For the glucose clamp procedure patients were connected to the Biostator (MTB Medizintechnik, Amstetten, Germany) for at least 2 hours prior to the start of the procedure. The Biostator automatically calculates the appropriate glucose infusion rate (GIR) to keep blood glucose at the target level. The patients remained fasting and in a supine or semi supine position during the entire glucose clamp. The patients were allowed to sip water throughout the clamp, but otherwise remained fasting.

For the continuous blood glucose concentration measurements, a peripheral vein in the hand or forearm of one arm was cannulated for insertion of an 18-gauge PTFE double lumen catheter, which is connected to the glucose sensor of the Biostator. A low dose heparin solution (10,000 Units heparin/100 mL saline) was infused to the tip of this catheter and taken up with the blood to prevent blood from clotting in the system. This hand remained under a heating pad throughout the trial. The heating of the hand resulted in an arterialization of the venous blood sampled by a retrograde catheter, due to a reflective opening of arterio-venous shunts. Blood samples for serum insulin analyses were drawn from a second 18-gauge catheter in the cubital vein of the same arm, the line being kept patent with 0.15 mM saline.

Another vein in the contralateral forearm was cannulated with an 18-gauge PTFE catheter for infusion of 20% glucose (D20W), [6,6-2H2] glucose, and insulin by infusion pumps.

Two serial insulin infusion rates (Step 1 and Step 2) were applied and each insulin infusion phase lasted approximately 180 minutes. The last 30 minutes of each insulin infusion phase was regarded as steady-state.

Step 1: Suppression of hepatic glucose production. During Step 1 and 2 of the clamp, D20W was enriched with 2.5-3% [6,6-2H2] glucose. Insulin (Humulin R U100, Eli Lilly& Co., Indianapolis, Ind., USA) was infused IV by means of a precision pump for 180 min at a rate of 30 mU/m2/min. This raised the plasma insulin concentration to a level suitable for examining the sub-maximal suppression of hepatic glucose production. Examining hepatic glucose production in Step 1 can illustrate the effect of a drug on hepatic insulin sensitivity.

Step 2: Stimulation of glucose disposal. After 180 minutes (end of Step 1), the insulin infusion was increased to 150 mU/m2/min for a further 180 minutes (Step 2) of the clamp. This provided supra-physiological insulin concentrations (approximately 400 uU/mL) that near maximally stimulated glucose disposal (primarily into skeletal muscle) and near maximally suppressed endogenous glucose production. By stimulating glucose disposal into peripheral tissues and organs, physiological markers measured during Step 2 can illustrate the effect of a drug on peripheral insulin sensitivity.

The glucose infusion rate (GIR; 20% v/v) required to maintain arterialized venous blood glucose (glucose oxidase method) at the target level of 110 mg/dL was recorded throughout the clamp. The steady-state period for insulin sensitivity measurements is defined as the time from 150-180 minutes following the initiation of the continuous insulin infusion during each step, and the GIR recorded during the last 30 minutes (steady-state) of each insulin infusion step was used for the determination of insulin sensitivity.

Blood samples for the determination of plasma glucose were drawn at scheduled time points before and during the clamp. The Biostator was recalibrated at regular intervals (approximately every 30 minutes and approximately every 10 minutes during steady state) by means of a reference method (YSI 2300 Stat). Blood for YSI measurement was drawn at the same time as the Biostator sampling, if possible. Samples were taken within ±5 minutes of the planned time.

The clamp procedure terminated 6 hours after the initiation of Step 1. The insulin infusion was discontinued after the last blood sample was collected. After completion of the clamp procedure, patients were fed a standardized lunch. Blood glucose continued to be monitored at the discretion of the investigator. Additional lab testing was done at the discretion of the Investigator for safety reasons (e.g., electrolytes, ECG, telemetry). Vital signs (including aural temperature) were monitored both pre-clamp and after the clamp.

Lipid Profile Interim Analysis

The results from day 91 (considered the primary endpoint) are presented in Table 2. Baseline is defined as the average of all assessments prior to the first dose. The results for changes in the lipid profile over time are presented in subsequent tables (values for days 127 and 176 reflect partial data available during the interim analysis). The results indicate the ApoC-III protein levels, fasting total triglyceride levels, and non-HDL-cholesterol levels were significantly reduced and HDL-cholesterol levels were significantly increased after treatment with ISIS 304801. There was a consistent reduction of triglyceride levels to less than 100 mg/dL, with an average of 70 mg/dL. There was rapid, robust, and durable treatment-dependent decreases in fasting VLDL-cholesterol and non-HDL-cholesterol. There was rapid, robust, and durable treatment-dependent increase in fasting HDL-cholesterol. Overall, ISIS 304801 treatment resulted in an improvement in the overall lipid profile of the patients.

TABLE 2

Lipid profile analysis (% change from baseline) at day 91

| | Placebo (n = 4) | 300 mg (n = 7) |
|---|---|---|
| Fasting ApoC-III | −7 | −88 |
| Fasting ApoB | −10 | −27 |
| Fasting HDL-Cholesterol | −7 | 40 |
| Fasting LDL-Cholesterol | −7 | −9 |
| Fasting non-HDL-cholesterol | −8 | −28 |
| Fasting total cholesterol | −7 | −14 |
| Fasting triglyceride | −10 | −72 |
| Fasting VLDL-ApoC-III | −8 | −92 |
| Fasting VLDL-C | −13 | −77 |

TABLE 3

Fasting ApoC-III protein levels (% change from baseline) over time

| Day | Placebo (n = 4) | 300 mg (n = 7) |
|---|---|---|
| 8 | −20 | −63 |
| 15 | 4 | −74 |
| 29 | −1 | −86 |
| 57 | −11 | −86 |
| 91 | −7 | −88 |
| 127 | −3 | −80 |
| 176 | 26 | −53 |

TABLE 4

Fasting ApoB protein levels (% change from baseline) over time

| Day | Placebo (n = 4) | 300 mg (n = 7) |
|---|---|---|
| 8 | −6 | −20 |
| 15 | 3 | −17 |
| 29 | −2 | −22 |
| 57 | −4 | −20 |
| 91 | −10 | −27 |
| 127 | −9 | −29 |
| 176 | 12 | −14 |

TABLE 5

Fasting HDL-Cholesterol levels (% change from baseline) over time

| Day | Placebo (n = 4) | 300 mg (n = 7) |
|---|---|---|
| 8 | 3 | 19 |
| 15 | 6 | 32 |
| 29 | 1 | 45 |
| 57 | −3 | 48 |
| 91 | −7 | 40 |
| 127 | 12 | 45 |
| 176 | 0 | 33 |

TABLE 6

Fasting LDL-Cholesterol levels (% change from baseline) over time

| Day | Placebo (n = 4) | 300 mg (n = 7) |
|---|---|---|
| 8 | 5 | −10 |
| 15 | 8 | −7 |
| 29 | −1 | −7 |
| 57 | 2 | −2 |
| 91 | −7 | −9 |
| 127 | −9 | −19 |
| 176 | 15 | 0 |

TABLE 7

Fasting non-HDL-Cholesterol levels (% change from baseline) over time

| Day | Placebo (n = 4) | 300 mg (n = 7) |
|---|---|---|
| 8 | −3 | −24 |
| 15 | 3 | −21 |
| 29 | −3 | −27 |
| 57 | −4 | −23 |
| 91 | −8 | −28 |
| 127 | −10 | −33 |
| 176 | 13 | −13 |

TABLE 8

Fasting Total Cholesterol levels (% change from baseline) over time

| Day | Placebo (n = 4) | 300 mg (n = 7) |
|---|---|---|
| 8 | −2 | −15 |
| 15 | 4 | −10 |
| 29 | −2 | −13 |
| 57 | −4 | −8 |
| 91 | −7 | −14 |
| 127 | −6 | −19 |
| 176 | 10 | −6 |

TABLE 9

Fasting triglyceride levels (% change from baseline) over time

| Day | Placebo (n = 4) | 300 mg (n = 7) |
|---|---|---|
| 8 | −29 | −55 |
| 15 | −12 | −54 |
| 29 | −9 | −72 |
| 57 | −24 | −71 |
| 91 | −10 | −72 |
| 127 | −14 | −66 |
| 176 | 5 | −47 |

TABLE 10

Fasting VLDL-ApoC-III levels (% change from baseline) over time

| Day | Placebo (n = 4) | 300 mg (n = 7) |
|---|---|---|
| 8 | −19 | −60 |
| 15 | −5 | −73 |
| 29 | 5 | −87 |
| 57 | −11 | −84 |
| 91 | −8 | −92 |
| 127 | −1 | −85 |
| 176 | 28 | −51 |

TABLE 11

Fasting VLDL levels (% change from baseline) over time

| Day | Placebo (n = 4) | 300 mg (n = 7) |
|---|---|---|
| 8 | −31 | −61 |
| 15 | −15 | −53 |
| 29 | −9 | −68 |
| 57 | −25 | −80 |
| 91 | −13 | −77 |
| 127 | −27 | −71 |
| 176 | 10 | −60 |

Diabetes Profile Interim Analysis

Baseline is defined as the first clamp before the first dose. Values for days 127 and 176 reflect partial data available during the interim analysis. The various parameters, insulin sensitivity index, glucose disposal rate during steady state, glucose metabolic clearance rate during steady state, the ratio of glucose metabolism to insulin, and suppression of hepatic glucose production were measured on day 92. The results for changes in the diabetes profile over time are presented in Table 12.

Plasma glucose, serum insulin, serum C-peptide, and NEFA AUCs (area under the curve) during MMTT was measured on day 91 and are presented in Table 13. Baseline is defined as the first mixed meal tolerance test (MMTT) before the first dose.

The levels of fasting glucose, glycosylated albumin, fructosamine, glycosylated hemoglobin over time were measured and are presented in Tables 14 and 15. Baseline, for parameters other than glucose, is defined as the last value prior to the first dose. The baseline for glucose is defined as the last value on or prior to Day −2.

The results demonstrate that ISIS 304801 treatment decreased free fatty acid, glycated albumin, fructosamine, and HbA1C levels. Treatment also resulted in improved measures in the diabetic profile by improving insulin sensitivity index and measures of peripheral insulin sensitivity, such as glucose disposal rate, glucose metabolism rate, and the ratio of glucose metabolism to insulin, and a measure of hepatic insulin sensitivity (suppression of hepatic glucose production). The data indicates that treatment with ISIS 304801 improved insulin sensitivity and ameliorated diabetes symptoms in the patients.

TABLE 12

Diabetes profile (% change from baseline) at day 92

|  | Placebo (n = 4) | 300 mg (n = 4) |
|---|---|---|
| Insulin sensitivity index | 1.2 | 32.7 |
| Glucose disposal rate during steady state, step 1 | 5.9 | 25.0 |
| Glucose disposal rate during steady state, step 2 | −0.3 | 22.6 |
| Glucose metabolic clearance rate (MCR) during steady state, step 1 | 8.7 | 25.6 |
| Glucose metabolic clearance rate (MCR) during steady state, step 2 | −1.1 | 20.6 |
| Glucose metabolism: insulin ratio during steady state, step 1 | 2.2 | 18.8 |
| Glucose metabolism: insulin ratio during steady state, step 2 | 1.9 | 30.2 |
| Suppression of hepatic glucose production, step 1 | 6.2 | 15.8 |
| Suppression of hepatic glucose production, step 2 | 3.1 | −5.7 |

TABLE 13

AUC profile of various serum parameters (% change from baseline) at day 91

|  | Placebo (n = 4) | 300 mg (n = 7) |
|---|---|---|
| Serum C-peptide | −16.3 | 17.1 |
| Free fatty acids | 9.5 | −9.3 |
| Serum insulin | −25.6 | 23.4 |
| Plasma glucose | 0.6 | −1.0 |

TABLE 14

Levels of fasting blood parameters (% change from baseline)

|  | Days | Placebo (n = 4) | 300 mg (n = 7) |
|---|---|---|---|
| Glycated albumin | 91 | 4.7 | −9.5 |
|  | 127 | 15.7 | −22.2 |
|  | 176 | 15.8 | −10.6 |
| Fructosamine | 91 | 5.9 | −13.6 |
|  | 127 | 30.9 | n.d. |
|  | 176 | 23.2 | −0.6 |
| Hemoglobin A1C | 91 | 6.5 | −3.3 |
|  | 127 | 10.9 | n.d. |
|  | 176 | 12.4 | −8.4 |

TABLE 15

Levels of fasting glucose (% change from baseline)

| Days | Placebo (n = 4) | 300 mg (n = 7) |
|---|---|---|
| 8 | −9.9 | −9.2 |
| 15 | −1.9 | −10.2 |
| 29 | −9.7 | −1.5 |
| 57 | −8.2 | −9.9 |
| 90 | 9.8 | −1.1 |
| 127 | −0.8 | −6.6 |
| 176 | 11.5 | −13.1 |

Based on these highly favorable results observed in Type 2 diabetes patients, ISIS 304801 may represent a new therapeutic opportunity for the treatment of insulin resistance and hypertriglyceridemia.

Example 2: Updated Data from the ISIS 304801 Phase II Clinical Trial

Example 1 discloses data from an interim analysis of the Phase II clinical trial. Example 2 discloses data from the same clinical trial disclosed in Example 1 updated with data from additional patients.

TABLE 1A

Baseline characteristics of patients in the Phase 2 study

|  | Placebo (n = 5) | 300 mg (n = 10) |
|---|---|---|
| Gender (M:F) | 2:3 | 2:8 |
| Age (yrs) | 55 | 57.2 |
| BMI (kg/m$^2$) | 32.5 | 33.4 |
| Fasting Glucose (mg/dL) | 180.2 | 180.9 |
| HbA1c (%) | 7.6 | 8.0 |
| Fasting Lipids & Lipoproteins, mg/dL | | |
| ApoC-III (mg/dL) | 11.5 | 13.7 |
| Triglycerides (mg/dL) | 215.2 | 266.3 |
| HDL-C (ppt; mg/dL) | 38 | 40.9 |
| Non-HDL-C (calc; mg/dL) | 175.2 | 172.5 |
| Apo B (mg/dL) | 119.2 | 113.9 |
| LDL-C (ultacent; mg/dL) | 134.3 | 121.3 |
| Total Cholesterol (mg/dL) | 213.2 | 213.4 |
| VLDL-ApoC-III (mg/dL) | 6.0 | 7.2 |
| VLDL-C (mg/dL) | 40.9 | 51.2 |

Lipid Profile Analysis

The results from day 91 (considered the primary endpoint) are presented in Table 2A. Baseline is defined as the average of all assessments prior to the first dose. The results for changes in the lipid profile over time are presented in subsequent tables. The results indicate the ApoC-III protein levels, fasting total triglyceride levels, and non-HDL-cholesterol levels were significantly reduced and HDL-cholesterol levels were significantly increased after treatment with ISIS 304801. There was a consistent reduction of triglyceride levels to less than 100 mg/dL, with an average of 70 mg/dL. There was rapid, robust, and durable treatment-dependent decreases in fasting VLDL-cholesterol and non-HDL-cholesterol. There was rapid, robust, and durable treatment-dependent increase in fasting HDL-cholesterol. Overall, ISIS 304801 treatment resulted in an improvement in the overall lipid profile of the patients.

TABLE 2A

Lipid profile analysis (% change from baseline) at day 91

|  | Placebo (n = 4) | 300 mg (n = 9) |
|---|---|---|
| Fasting ApoC-III | −7 | −88 |
| Fasting ApoB | −10 | −21 |
| Fasting HDL-Cholesterol | −7 | 42 |
| Fasting LDL-Cholesterol | −7 | −0.2 |
| Fasting non-HDL-cholesterol | −8 | −22 |
| Fasting total cholesterol | −7 | −9 |
| Fasting triglyceride | −10 | −69 |
| Fasting VLDL-ApoC-III | −8 | −90 |
| Fasting VLDL-C | −13 | −73 |

TABLE 3A

Fasting ApoC-III protein levels (% change from baseline) over time

| Day | Placebo (n = 4) | 300 mg (n = 9) |
|---|---|---|
| 8 | −20 | −61 |
| 15 | 4 | −75 |
| 29 | −1 | −86 |
| 57 | −11 | −87 |
| 91 | −7 | −88 |
| 127 | −0.3 | −80 |
| 176 | 14 | −56 |

TABLE 4A

Fasting ApoB protein levels (% change from baseline) over time

| Day | Placebo (n = 4) | 300 mg (n = 9) |
|---|---|---|
| 8 | −6 | −15 |
| 15 | 3 | −14 |
| 29 | −2 | −20 |
| 57 | −4 | −18 |
| 91 | −10 | −21 |
| 127 | −9 | −21 |
| 176 | 11 | −13 |

TABLE 5A

Fasting HDL-Cholesterol levels (% change from baseline) over time

| Day | Placebo (n = 4) | 300 mg (n = 9) |
|---|---|---|
| 8 | 3 | 21 |
| 15 | 6 | 35 |
| 29 | 1 | 47 |
| 57 | −3 | 48 |
| 91 | −7 | 42 |
| 127 | 10 | 56 |
| 176 | 1 | 45 |

TABLE 6A

Fasting LDL-Cholesterol levels (% change from baseline) over time

| Day | Placebo (n = 4) | 300 mg (n = 9) |
|---|---|---|
| 8 | 5 | −5 |
| 15 | 8 | −2 |
| 29 | −1 | −4 |
| 57 | 2 | 4 |
| 91 | −7 | −0.2 |
| 127 | −10 | −10 |
| 176 | 15 | −1 |

TABLE 7A

Fasting non-HDL-Cholesterol levels (% change from baseline) over time

| Day | Placebo (n = 4) | 300 mg (n = 9) |
|---|---|---|
| 8 | −3 | −20 |
| 15 | 3 | −18 |
| 29 | −3 | −25 |
| 57 | −4 | −19 |
| 91 | −8 | −22 |
| 127 | −9 | −28 |
| 176 | 11 | −16 |

TABLE 8A

Fasting Total Cholesterol levels (% change from baseline) over time

| Day | Placebo (n = 4) | 300 mg (n = 9) |
|---|---|---|
| 8 | −2 | −12 |
| 15 | 4 | −8 |
| 29 | −2 | −11 |
| 57 | −4 | −6 |
| 91 | −7 | −9 |
| 127 | −6 | −12 |
| 176 | 9 | −5 |

TABLE 9A

Fasting triglyceride levels (% change from baseline) over time

| Day | Placebo (n = 4) | 300 mg (n = 9) |
|---|---|---|
| 8 | −29 | −52 |
| 15 | −12 | −55 |
| 29 | −9 | −71 |
| 57 | −24 | −70 |
| 91 | −10 | −69 |
| 127 | −10 | −66 |
| 176 | 1 | −51 |

TABLE 10A

Fasting VLDL-ApoC-III levels (% change from baseline) over time

| Day | Placebo (n = 4) | 300 mg (n = 9) |
|---|---|---|
| 8 | −19 | −63 |
| 15 | −5 | −74 |
| 29 | 5 | −88 |
| 57 | −11 | −85 |
| 91 | −8 | −90 |
| 127 | −3 | −86 |
| 176 | 12 | −63 |

TABLE 11A

Fasting VLDL levels (% change from baseline) over time

| Day | Placebo (n = 4) | 300 mg (n = 9) |
|---|---|---|
| 8 | −31 | −56 |
| 15 | −15 | −56 |
| 29 | −9 | −66 |
| 57 | −25 | −75 |
| 91 | −13 | −73 |
| 127 | −14 | −71 |
| 176 | 4 | −53 |

Diabetes Profile Analysis

The results demonstrate that ISIS 304801 treatment decreased free fatty acid, glycated albumin, fructosamine, and HbA1C levels. Treatment also resulted in improved measures in the diabetic profile by improving insulin sensitivity index and measures of peripheral insulin sensitivity, such as glucose disposal rate, glucose metabolism rate, and the ratio of glucose metabolism to insulin, and a measure of hepatic insulin sensitivity (suppression of hepatic glucose production). The data indicates that treatment with ISIS 304801 improved insulin sensitivity and ameliorated diabetes symptoms in the patients.

TABLE 12A

Diabetes profile (% change from baseline) at day 92

|  | Placebo (n = 4) | 300 mg (n = 6) |
|---|---|---|
| Insulin sensitivity index | 1.2 | 52.6 |
| Glucose disposal rate during steady state, step 1 | 5.8 | 6.3 |
| Glucose disposal rate during steady state, step 2 | −0.3 | 12.7 |
| Glucose metabolic clearance rate (MCR) during steady state, step 1 | 8.6 | 7.0 |
| Glucose metabolic clearance rate (MCR) during steady state, step 2 | −1.0 | 12.0 |
| Glucose metabolism: insulin ratio during steady state, step 1 | 2.2 | 1.4 |
| Glucose metabolism: insulin ratio during steady state, step 2 | 1.9 | 24.0 |
| Suppression of hepatic glucose production, step 1 | 6.3 | 6.2 |
| Suppression of hepatic glucose production, step 2 | 3.1 | −2.5 |

TABLE 13A

AUC profile of various serum parameters (% change from baseline) at day 91

|  | Placebo (n = 4) | 300 mg (n = 9) |
|---|---|---|
| Serum C-peptide | −16.3 | 16.6 |
| Free fatty acids | 9.5 | −7.0 |
| Serum insulin | −25.6 | 16.7 |
| Plasma glucose | 0.6 | −3.5 |

TABLE 14A

Levels of fasting blood parameters (% change from baseline)

|  | Days | Placebo (n = 4) | 300 mg (n = 9) |
|---|---|---|---|
| Glycated albumin | 91 | 4.7 | −10.4 |
|  | 127 | 6.3 | −14.0 |
|  | 176 | 11.4 | −13.6 |
| Fructosamine | 91 | 5.9 | −13.8 |
|  | 127 | 22.0 | −1.8 |
|  | 176 | 19.5 | −4.0 |
| Hemoglobin A1C | 91 | 6.5 | −3.1 |
|  | 127 | 9.0 | −3.5 |
|  | 176 | 10.0 | −5.5 |

TABLE 15A

Levels of fasting glucose (% change from baseline)

| Days | Placebo (n = 4) | 300 mg (n = 9) |
|---|---|---|
| 8 | −9.9 | −13.1 |
| 15 | −1.9 | −13.2 |
| 29 | −9.7 | −8.0 |
| 57 | −8.2 | −14.3 |
| 90 | 9.8 | −7.2 |
| 127 | −9.0 | −15.1 |
| 176 | −0.7 | −21.3 |

Based on these highly favorable results observed in Type 2 diabetes patients, ISIS 304801 represents a new therapeutic opportunity for the treatment of hypertriglyceridemia in diabetic or pre-diabetic patients.

The invention claimed is:

1. A method of improving glucose control of a subject comprising administering a compound comprising an antisense oligonucleotide 12-30 nucleobases in length targeting ApoCIII, wherein the subject has moderately controlled diabetes or uncontrolled diabetes, and is on a stable dose of a glucose lowering agent and, upon administration of the compound, the subject exhibits reduced HbA1c, thereby improving the glucose control of the subject.

2. The method of claim 1, wherein the subject is on a stable dose of metformin.

3. The method of claim 1, wherein the subject has fasting triglyceride levels 200 and 500 mg/dl.

4. The method of claim 1, wherein ApoCIII has a nucleic acid sequence as shown in SEQ ID NO: 1 or SEQ ID NO: 2.

5. The method of claim 4, wherein the antisense oligonucleotide has a nucleobase sequence comprising at least 8 contiguous nucleobases of a nucleobase sequence of SEQ ID NO: 4.

6. The method of claim 4, wherein the antisense oligonucleotide consists of a nucleobase sequence of SEQ ID NO: 4.

7. The method of claim 4, wherein the nucleobase sequence of the antisense oligonucleotide is at least 80%, at least 90% or 100% complementary to a nucleobase sequence of SEQ ID NO: 1 or SEQ ID NO: 2.

8. The method of claim 1, wherein the antisense oligonucleotide consists of a single-stranded modified oligonucleotide.

9. The method of claim 1, wherein the antisense oligonucleotide consists of 20 linked nucleosides.

10. The method of claim 1, wherein the antisense oligonucleotide has at least one modified internucleoside linkage, sugar moiety or nucleobase.

11. The method of claim 10, wherein the internucleoside linkage of the antisense oligonucleotide is a phosphorothioate internucleoside linkage, the modified sugar is a bicyclic sugar or 2'-O-methoxyethyl and the modified nucleobase is a 5-methylcytosine.

12. The method of claim 1, wherein the antisense oligonucleotide comprises:
(a) a gap segment consisting of linked deoxynucleosides;
(b) a 5' wing segment consisting of linked nucleosides;
(c) a 3' wing segment consisting linked nucleosides;
wherein the gap segment is positioned immediately adjacent to and between the 5' wing segment and the 3' wing segment and wherein each nucleoside of each wing segment comprises a modified sugar.

13. The method of claim 1, wherein the antisense oligonucleotide comprises:
(a) a gap segment consisting of 10 linked deoxynucleosides;
(b) a 5' wing segment consisting of 5 linked nucleosides;
(c) a 3' wing segment consisting 5 linked nucleosides;
wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, and wherein each internucleoside linkage is a phosphorothioate linkage.

14. A method of improving glucose control in a subject comprising, selecting a subject with moderately controlled diabetes or uncontrolled diabetes, who is on a stable dose of a glucose lowering agent, and administering to the subject a therapeutically effective amount of a compound comprising an antisense oligonucleotide having the sequence of SEQ ID NO: 4 wherein the antisense oligonucleotide comprises:
(a) a gap segment consisting of 10 linked deoxynucleosides;
(b) a 5' wing segment consisting of 5 linked nucleosides;
(c) a 3' wing segment consisting 5 linked nucleosides;
wherein the gap segment is positioned immediately adjacent to and between the 5' wing segment and the 3' wing segment, wherein each nucleoside of each wing segment comprises a 2'-O-methoxyethyl sugar, wherein each cytosine is a 5-methylcytosine, wherein each internucleoside linkage is a phosphorothioate linkage, and wherein upon administration of the compound, the subject exhibits reduced HbA1c, thereby improving the glucose control in the subject.

15. The method of claim 1, wherein the antisense oligonucleotide is parenterally administered.

16. The method of claim 15, wherein the parenteral administration is subcutaneous administration.

17. The method of claim 1, further comprising administration of the glucose lowering agent to the subject.

18. The method of claim 17, wherein the glucose lowering agent is metformin.

19. The method of claim 17, wherein the glucose lowering agent is administered concomitantly or sequentially with the antisense oligonucleotide.

20. The method of claim 1, wherein the antisense oligonucleotide is a salt form.

21. The method of claim 1, wherein the compound is in a composition comprising a pharmaceutically acceptable carrier or diluent.

22. The method of claim 1, wherein the subject has triglyceride levels ≥500 mg/dl.

23. The method of claim 1, wherein the reduction in HbA1c is a reduction of at least 3% to at least 8% compared to baseline levels of HbA1c.

24. The method of claim 1, wherein the subject has triglyceride levels between 200 and 499 mg/dl.

25. The method of claim 23, wherein the subject has fasting triglyceride levels ≥200 and ≤500 mg/dl.

26. The method of claim 1, wherein the subject has triglyceride levels of at least 150 m g/dl.

27. The method of claim 1, wherein the subject has moderately controlled diabetes and an HbA1c level of 7% to 9%.

28. The method of claim 1, wherein the subject has uncontrolled diabetes and an HbA1c level greater than 9%.

29. The method of claim 1, wherein upon administration of the compound, the subject exhibits changes in one or more physiological markers, wherein the changes are selected from among one or more of:
insulin sensitivity index, glucose disposal rate, glucose MCR and/or glucose metabolism:insulin ration is improved;
free fatty acids, triglycerides, non-HDL-C, VLDL-C, ApoCIII containing VLDL, ApoB and/or LDL-C is reduced; and
HDL-C is increased.

* * * * *